United States Patent
Nakagawa et al.

(10) Patent No.: US 10,478,914 B2
(45) Date of Patent: Nov. 19, 2019

(54) METHOD FOR BUTT WELDING, BUTT WELDED JOINT, AND OUTSIDE JOINT MEMBER FOR CONSTANT VELOCITY UNIVERSAL JOINT

(71) Applicants: Naoki Nakagawa, Shizuoka (JP); Shintaro Suzuki, Shizuoka (JP); Kenichi Nakano, Shizuoka (JP); Takuya Fujita, Shizuoka (JP); Kiyohiro Suzuki, Shizuoka (JP); Renji Natsume, Shizuoka (JP); Tatsuro Sugiyama, Shizuoka (JP); Masazumi Kobayashi, Shizuoka (JP)

(72) Inventors: Naoki Nakagawa, Shizuoka (JP); Shintaro Suzuki, Shizuoka (JP); Kenichi Nakano, Shizuoka (JP); Takuya Fujita, Shizuoka (JP); Kiyohiro Suzuki, Shizuoka (JP); Renji Natsume, Shizuoka (JP); Tatsuro Sugiyama, Shizuoka (JP); Masazumi Kobayashi, Shizuoka (JP)

(73) Assignee: NTN CORPORATION, Osaka (JP)

( * ) Notice: Subject to any disclaimer, the term of this patent is extended or adjusted under 35 U.S.C. 154(b) by 355 days.

(21) Appl. No.: 15/319,097

(22) PCT Filed: May 20, 2015

(86) PCT No.: PCT/JP2015/064518
§ 371 (c)(1),
(2) Date: Dec. 15, 2016

(87) PCT Pub. No.: WO2015/194308
PCT Pub. Date: Dec. 23, 2015

(65) Prior Publication Data
US 2017/0120369 A1 May 4, 2017

(30) Foreign Application Priority Data

Jun. 18, 2014 (JP) .................................. 2014-125500

(51) Int. Cl.
*B23K 10/00* (2006.01)
*B23K 15/00* (2006.01)
(Continued)

(52) U.S. Cl.
CPC .......... *B23K 15/0046* (2013.01); *B23K 15/04* (2013.01); *B23K 26/0823* (2013.01);
(Continued)

(58) Field of Classification Search
CPC .. B23K 15/0046; B23K 26/21; B23K 26/282; B23K 15/04; B23K 26/0823;
(Continued)

(56) References Cited

U.S. PATENT DOCUMENTS 2,604,569 A * 7/1952 Denneen .............. B23K 33/006
219/105
5,601,736 A * 2/1997 Saitoh .................... B23K 26/26
219/121.64
(Continued)

FOREIGN PATENT DOCUMENTS

JP 63-260685 10/1988
JP 2006-289500 10/2006
(Continued)

OTHER PUBLICATIONS

International Search Report dated Aug. 25, 2015 in International (PCT) Application No. PCT/JP2015/064518.
(Continued)

*Primary Examiner* — Mark H Paschall
(74) *Attorney, Agent, or Firm* — Wenderoth, Lind & Ponack, L.L.P.

(57) ABSTRACT

For butt-welding, which includes bringing joining end surfaces of a cup member and a shaft member into abutment against each other and radiating a high energy intensity beam from a radially outer side, the shaft member has a recess on a radially inner side of the joining end surface to obtain a welded portion having a closed hollow cavity on a radially inner side after butt-welding. The joining end surface (protruding surface) of the cup member protrudes toward a radially inner side with respect to an inner diameter of the joining end surface of the shaft member. With this, a welded portion of an outer joint member of a constant velocity universal joint, which is manufactured by joining the cup member and the shaft member, can be improved in strength and quality.

12 Claims, 24 Drawing Sheets

(51) Int. Cl.

| | |
|---|---|
| *B23K 26/21* | (2014.01) |
| *F16D 3/205* | (2006.01) |
| *F16D 3/223* | (2011.01) |
| *B23K 15/04* | (2006.01) |
| *B23K 26/08* | (2014.01) |
| *B23K 33/00* | (2006.01) |
| *G01N 29/04* | (2006.01) |
| *G01N 29/22* | (2006.01) |
| *G01N 29/28* | (2006.01) |
| *B23K 26/282* | (2014.01) |
| *F16D 1/027* | (2006.01) |
| *F16D 3/227* | (2006.01) |
| *B23K 101/04* | (2006.01) |
| *B23K 103/04* | (2006.01) |
| *B23K 103/18* | (2006.01) |

(52) U.S. Cl.
CPC ............ *B23K 26/21* (2015.10); *B23K 26/282* (2015.10); *B23K 33/006* (2013.01); *F16D 1/027* (2013.01); *F16D 3/205* (2013.01); *F16D 3/223* (2013.01); *F16D 3/227* (2013.01); *G01N 29/043* (2013.01); *G01N 29/225* (2013.01); *G01N 29/28* (2013.01); *B23K 2101/04* (2018.08); *B23K 2103/04* (2018.08); *B23K 2103/18* (2018.08); *F16D 3/2055* (2013.01); *F16D 2003/22326* (2013.01); *G01N 2291/267* (2013.01)

(58) Field of Classification Search
CPC .............. B23K 33/006; B23K 2103/18; B23K 2101/04; H05H 1/26; F16D 1/027; F16D 3/205; F16D 3/223; F16D 3/227; D16D 2003/22326; G01N 29/043; G01N 29/225; G01N 29/28; G01N 2003/22326
USPC .... 219/121.13, 121.14, 121.45, 121.46, 121, 219/63, 121.64, 137 R See application file for complete search history.

(56) References Cited

U.S. PATENT DOCUMENTS

| | | | |
|---|---|---|---|
| 2006/0231531 A1 | 10/2006 | Burnett et al. | |
| 2010/0331093 A1* | 12/2010 | Ozawa | B60B 27/00 464/139 |
| 2011/0291407 A1* | 12/2011 | McDermott | B23K 31/027 285/286.1 |
| 2014/0291301 A1 | 10/2014 | Tosaji et al. | |
| 2016/0184930 A1 | 6/2016 | Murata et al. | |
| 2016/0201730 A1 | 7/2016 | Osugi et al. | |

FOREIGN PATENT DOCUMENTS

| | | |
|---|---|---|
| JP | 2011-112039 | 6/2011 |
| JP | 2012-57696 | 3/2012 |
| WO | 2013/069433 | 5/2013 |
| WO | 2015/029682 | 3/2015 |
| WO | 2015/107981 | 7/2015 |

OTHER PUBLICATIONS

International Preliminary Report on Patentabiltity and Written Opinion of the International Searching Authority dated Dec. 20, 2016 in International (PCT) Application No. PCT/JP2015/064518.
Nikkan Kogyo Shimbun, Ltd., Website Article, http://www.nikkan.co.jp/news/nkx0420140521beaj.html, May 21, 2014, with English statement of relevance.
NTN Corporation, Website Article, http://www.ntn.co.jp/japan/news/new_products/news201400038.html, May 22, 2014, with English statement of relevance.
Nikkei Business Publications, Inc., Website Article, http://techon.nikkeibp.co.jp/article/EVENT/20140522/353568, May 22, 2014, with English statement of relevance.
Sanpo Publications, Inc., Website Article, http://www.sanpo-pub.co.jp/topnews/2014/0523016259.html, Jun. 5, 2014, with English statement of relevance.
Mechanical-Tech, Inc., Website Article, http://mechanical-tech.jp/node/5915, May 24, 2014, with English statement of relevance.
IID, Inc., Website Article, http://response.jp/article/2014/05/26/223911.html, May 26, 2014, with English statement of relevance.
Carview Corporation, Website Article, http://carview.yahoo.co.jp/news/market/20140526-10204741-carview, May 26, 2014, with English statement of relevance.
Yahoo Japan Corporation, Website Article, http://headlines.yahoo.co.jp/hl?a=20140526-00000002-rps-bus_all, May 26, 2014, with English statement of relevance.
Nikkan Kogyo Shimbun Ltd, Published Article, May 21, 2014, with English statement of relevance.
Nikkei Inc., Published Article, May 22, 2014, with English statement of relevance.
Nikkan Jidosha Shimbun Inc., Published Article, May 26, 2014, with English statement of relevance.
NTN Corporation, Exhibition at the Automotive Engineering Exposition 2014, Society of Automotive Engineers of Japan, Inc., Pacifico Yokohama, May 21-23, 2014, with English statement of relevance.

\* cited by examiner

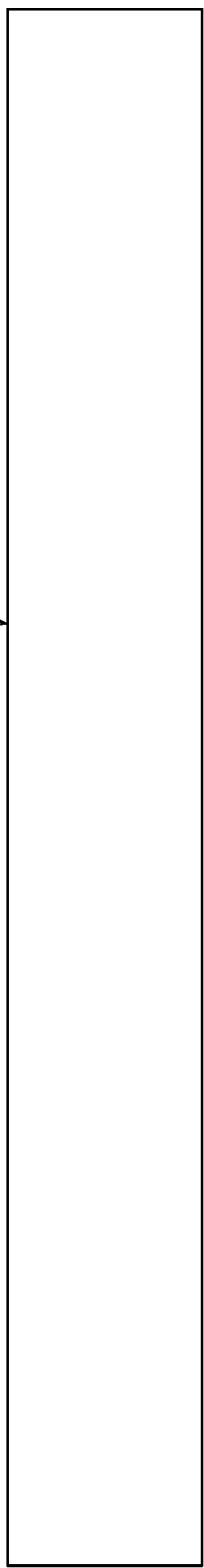
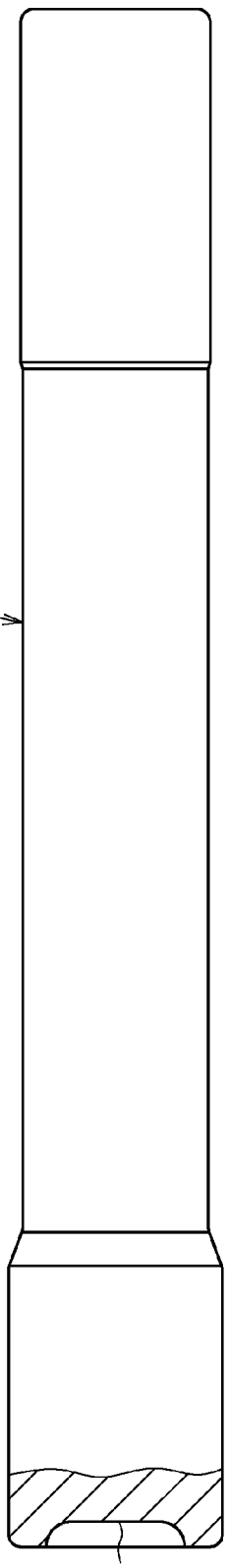
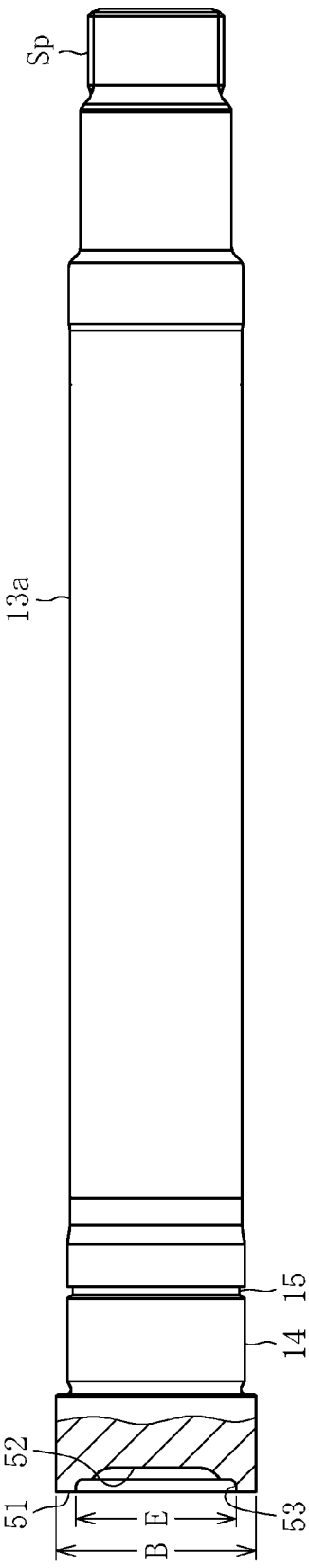

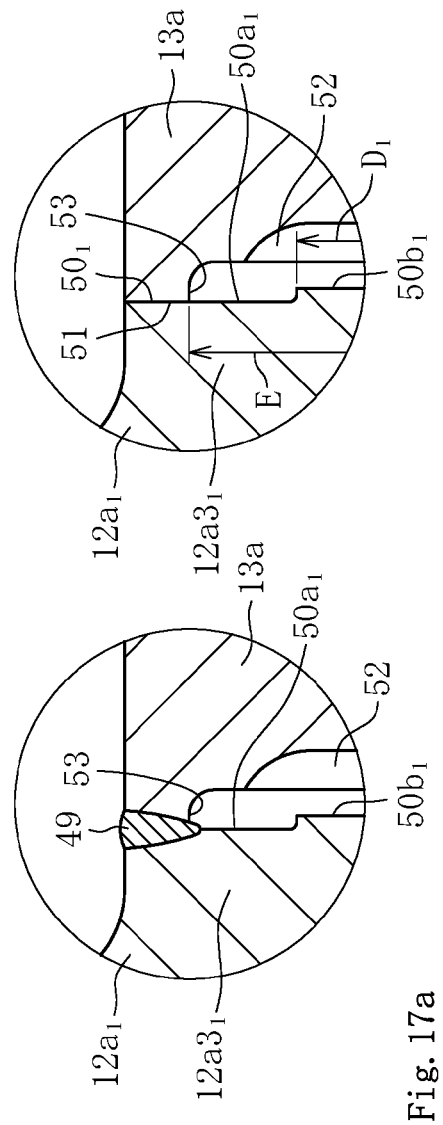
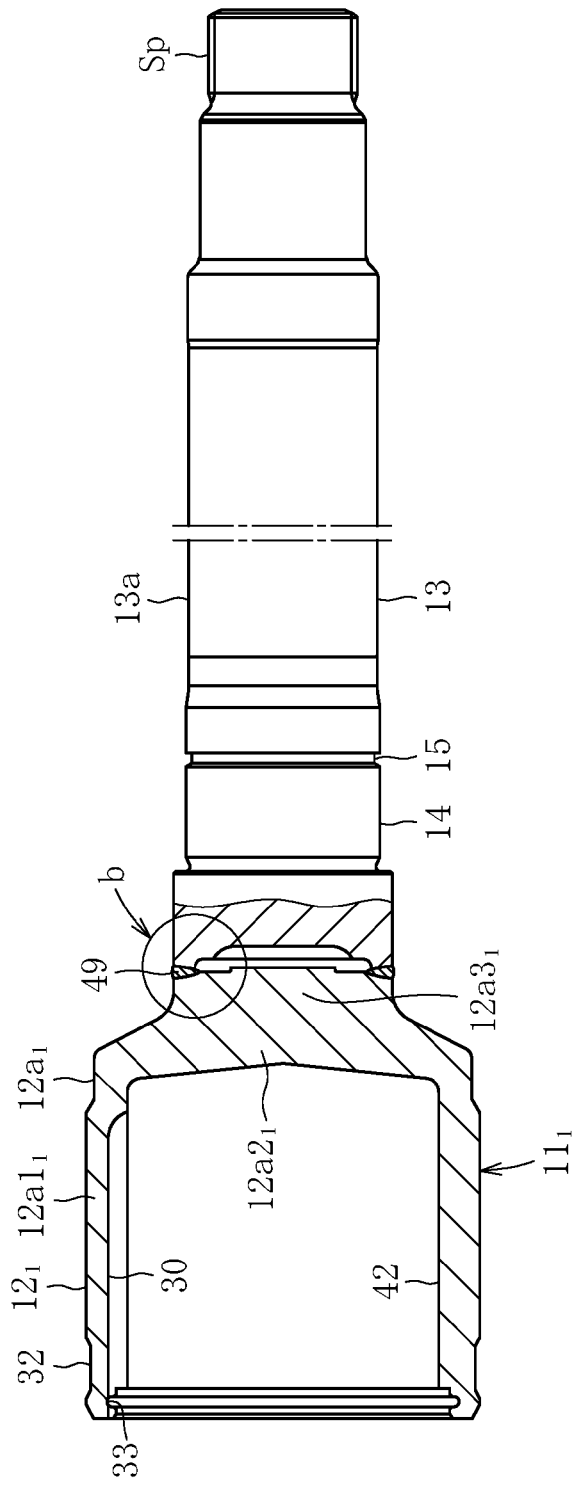

METHOD FOR BUTT WELDING, BUTT WELDED JOINT, AND OUTSIDE JOINT MEMBER FOR CONSTANT VELOCITY UNIVERSAL JOINT

TECHNICAL FIELD

The present invention relates to a method of butt-welding and a butt-welded joint for use in, for example without limitation, manufacturing an outer joint member of a constant velocity universal joint.

BACKGROUND ART

In a constant velocity universal joint, which is used to construct a power transmission system for automobiles and various industrial machines, two shafts on a driving side and a driven side are coupled to each other to allow torque transmission therebetween, and rotational torque can be transmitted at a constant velocity even when each of the two shafts forms an operating angle. The constant velocity universal joint is roughly classified into a fixed type constant velocity universal joint that allows only angular displacement, and a plunging type constant velocity universal joint that allows both the angular displacement and axial displacement. In a drive shaft configured to transmit power from an engine of an automobile to a driving wheel, for example, the plunging type constant velocity universal joint is used on a differential side (inboard side), and the fixed type constant velocity universal joint is used on a driving wheel side (outboard side).

Irrespective of the fixed type and the plunging type, the constant velocity universal joint includes, as main components, an inner joint member, an outer joint member, and torque transmission members. The outer joint member includes a cup section and a shaft section. The cup section has track grooves formed in an inner peripheral surface thereof and configured to allow the torque transmission members to roll thereon. The shaft section extends from a bottom of the cup section in an axial direction. In many cases, the outer joint member is constructed by integrally forming the cup section and the shaft section by subjecting a rod-like solid blank (bar member) to plastic working such as forging and ironing or processing such as cutting work, heat treatment, and grinding.

Incidentally, an outer joint member (long stem type) including a shaft section longer than a standard may sometimes be used. For example, in order to equalize lengths of a right part and a left part of the drive shaft, the long stem type is used for a constant velocity universal joint on the inboard side that corresponds to one side of the drive shaft. In this case, the shaft section is rotatably supported by a support bearing. Although varied depending on vehicle types, the length of the shaft section of the long stem type is approximately from 300 mm to 400 mm in general. The outer joint member of the long stem type has a long shaft section, and hence there is a difficulty in integrally forming the cup section and the shaft section with high accuracy. Therefore, there is known an outer joint member in which the cup section and the shaft section are formed as separate members, and both the members are joined through friction press-contact (Patent Literature 1).

An overview of the friction press-contact technology for the outer joint member described in Patent Literature 1 is described below. First, as illustrated in FIG. 23, a cup member 72 and a shaft member 73 are joined through the friction press-contact to form an intermediate product 71'. Next, burrs 75 on a radially outer side of a joining portion 74 are removed, and hence an outer joint member 71 as illustrated in FIG. 24 is obtained. The burrs 75 are generated on the joining portion 74 of the intermediate product 71' along with the press-contact. The burrs 75 on the radially outer side of the joining portion 74 are removed through processing such as turning. Accordingly, a support bearing (rolling bearing 6: see FIG. 1) to a shaft section of the outer joint member 71.

Although illustration is omitted, the intermediate product 71' is processed into a finished product of the outer joint member 71 through machining of a spline, snap ring grooves, and the like, and through heat treatment, grinding, and the like. Therefore, the outer joint member 71 and the intermediate product 71' have slight differences in shape. However, illustration of the slight differences in shape is omitted in FIG. 23 and FIG. 24 to simplify the description, and the outer joint member 71 being the finished product and the intermediate product 71' are denoted by the reference symbols at the same parts. The same applies to the description below.

CITATION LIST

Patent Literature 1: JP 2012-57696 A
Patent Literature 2: WO 2013/069433 A pamphlet
Patent Literature 3: JP 63-260685 A

SUMMARY OF INVENTION

Technical Problem

The burrs 75 on the joining portion 74, which are generated due to the friction press-contact, not only are quenched by friction heat and cooling that follows the friction heat to have a high hardness but also have a distorted shape extended in an axial direction and a radial direction. Therefore, when removing the burrs 75 on the radially outer side through the turning, a tip for turning is liable to be significantly abraded due to the high hardness and cracked due to the distorted shape. Therefore, it is difficult to increase the turning speed. In addition, a cutting amount per pass of the tip for turning is decreased, and hence the number of passes is increased, which causes a problem in that the cycle time is increased to increase the manufacturing cost.

Further, in order to inspect a joining state of the joining portion 74 of the outer joint member 71, when ultrasonic flaw detection, which enables flaw detection at high speed, is to be performed, an ultrasonic wave is scattered due to the burrs 75 remaining on the radially inner side of the joining portion 74, and hence the joining state cannot be checked. Therefore, there occurs a problem in that total inspection through the ultrasonic flaw detection cannot be performed after the joining.

In view of the above-mentioned problems, when welding through use of high energy intensity beam such as laser welding or electron beam welding is employed, it is conceivable that the surfaces of the joining portion may be prevented from being increased in thickness unlike the case of the friction press-contact (Patent Literature 2). However, as illustrated in FIG. 25, when the cup member 72 and the shaft member 73 are brought into abutment against each other to be welded, a hollow cavity portion 76 having a relatively large volume is formed. Then, a pressure in the hollow cavity portion 76 is increased due to processing heat during the welding, and after completion of the welding, the pressure is decreased. Due to such variation in the internal pressure of the hollow cavity portion 76, blowing of a molten material occurs. Thus, there arise defects such as formation of a recess on a surface of the welded portion, poor penetration depth, and generation of air bubbles inside the welded portion, thereby degrading the welding state. As a result, the strength of the welded portion is not stable, which adversely affects quality.

Further, in consideration of the case where members (workpieces) constructing the outer joint member of the constant velocity universal joint are to be welded, the workpieces employ medium to high carbon steel having a high carbon content to secure strength. Thus, when the workpieces are welded to each other as they are, the welded portion is significantly hardened, and becomes more liable to be cracked. Therefore, for the purpose of reducing the hardness and securing the toughness, pre-heating is performed to reduce the cooling rate after welding. However, when the workpieces each having a solid shaft shape are butt-welded as they are, a large volume in the periphery of the welded portion may cause a long time for pre-heating to be required. Thus, the cycle time is increased to increase the manufacturing cost.

Further, when an unjoined portion, that is, contact surface remains on the radially inner side of the welded portion, there is a risk of causing increase in notch factor and decrease in joint strength.

It is an object of the present invention to provide a method of butt-welding capable of eliminating the above-mentioned problems of the related-art butt-welding, and improving strength and quality of the welded portion of the outer joint member of the constant velocity universal joint which is manufactured by joining the cup member and the shaft member through butt-welding.

Solution to Problem

According to one embodiment of the present invention, there is provided a method of butt-welding, comprising: bringing a solid shaft-shaped end portion of a first workpiece and a solid shaft-shaped end portion of a second workpiece into abutment against each other; and radiating a high energy intensity beam from a radially outer side, wherein the second workpiece has a recess on a radially inner side of a joining end surface, and the first workpiece has a joining end surface protruding toward a radially inner side with respect to an inner diameter of the joining end surface of the second workpiece.

Herein, the term "solid shaft shape" is intended to exclude a shaft having a hollow cavity penetrating in an axial direction, or a shaft having an elongated hollow cavity portion extending from a joining end surface in the axial direction (see Patent Literatures 2 and 3). The cup member has a bottomed cylindrical shape as a whole, but the short shaft section having the joining end surface formed thereon does not have a through hole and an elongated hollow cavity portion extending from the joining end surface in the axial direction. Thus, at least the short shaft section has a solid shaft shape.

In general, the electron beam welding is performed in vacuum. Thus, the problems such as blowing of a molten material and generation of air bubbles are resolved. In Patent Literature 3, there is disclosed welding of hollow shafts through abutment in vacuum. However, such welding with the shafts formed into a hollow shape is performed for the purpose of reducing a mass and heat capacity, and is based on idea that is different from the idea of forming a shallow recess on a radially inner side of a joining end surface on an end portion having a solid shaft shape. A shaft having such shallow recess on the radially inner side of the joining end surface of the end portion having the solid shaft shape is still a solid shaft, and is not a hollow shaft. Therefore, the object of the invention disclosed in Patent Literature 3 cannot be achieved.

The technical significance of forming the recess on the radially inner side of the joining end surface is described below.

First, when the recess is formed, the joining end surface is formed into an annular surface, thereby reducing an area of the abutment surface to be welded, and also reducing the volume in the vicinity of the welded portion. Thus, when the pre-heating before welding or post-heating after welding is performed, a necessary joint portion can be efficiently heated. Therefore, the heating time can be reduced, and the manufacturing cost can be reduced. Further, also in the case of joining with a member of a different type number or type having a different joint outer diameter, especially a member having a large outer diameter of the joint portion, the diameter of the recess may be adjusted to cope with such case without increasing the cycle time.

Further, for butt-welding of end portions having a solid shaft shape, when the recess is formed on the radially inner side of the joining end surface, a closed hollow cavity is formed on the radially inner side of the welded portion after welding. As a result, there exists no unjoined portion on the radially inner side of the welded portion. Thus, the problem of decrease in welding strength due to the presence of the unwelded portion on the radially inner side of the welded portion can be resolved. Thus, stable welding strength can be secured.

Further, when the recess is formed on the radially inner side of the welded portion, the inner diameter portion of the recess provides a straight part in the axial direction. Thus, inspection of defects through ultrasonic flaw detection, especially detection of penetration depth can be performed. Further, an end surface of a workpiece which is different from the workpiece having the recess protrudes toward the radially inner side with respect to the inner diameter portion of the recess. Thus, when the ultrasonic flaw detection is performed, a transmission pulse from a probe is not reflected to the probe side, thereby enhancing inspection accuracy and reliability of the ultrasonic flaw detection.

As a matter of course, in welding with a high energy intensity beam, a bead width is small, and deep penetration can be obtained in a short period of time, thereby being capable of increasing the strength of the welded portion and reducing thermal strain. Further, burrs are not generated, and hence post-processing for the joining portion can be omitted. As a result, the manufacturing cost can be reduced. Further, there is no scattering of ultrasonic waves caused by the burrs, which is a problem raised in the case of joining through the friction press-contact. Thus, total inspection through ultrasonic flaw detection can be performed to stably secure high welding quality.

Advantageous Effects of Invention

As is clear from the description above, according to the method of butt-welding of the present invention, the strength and quality of the welded portion can be improved. Further, when the present invention is applied to manufacturing of an outer joint member of a constant velocity universal joint having the cup member and the shaft member joined through butt-welding, the outer joint member improved in strength and quality of the welded portion can be provided.

BRIEF DESCRIPTION OF DRAWINGS

FIG. 2a is an enlarged view for illustrating a first embodiment of the outer joint member of FIG. 1.

FIG. 2b is an enlarged view of a portion "b" of FIG. 2a.

FIG. 2c is an enlarged view, which is similar to FIG. 2b, for illustrating a state before welding.

FIG. 5a is a front view of a bar material being a blank of a shaft member.

FIG. 5b is a partial sectional front view after forging.

FIG. 5c is a partial sectional front view of the shaft member after turning and spline processing.

FIG. 17a is a partial sectional front view for illustrating a second embodiment of the outer joint member.

FIG. 17b is an enlarged view of a portion "b" of FIG. 17a.

FIG. 17c is an enlarged view, which is similar to FIG. 17b, for illustrating a state before welding.

FIG. 18 is a vertical sectional view of the cup member of FIG. 17a.

DESCRIPTION OF EMBODIMENTS

Now, description is made of embodiments of the present invention with reference to the drawings.

First, a first embodiment of an outer joint member is described with reference to FIG. 1 and FIG. 2a to FIG. 2c, and subsequently, a first embodiment of a method of manufacturing the outer joint member is described with reference to FIG. 3 to FIG. 16.

Figure 1:
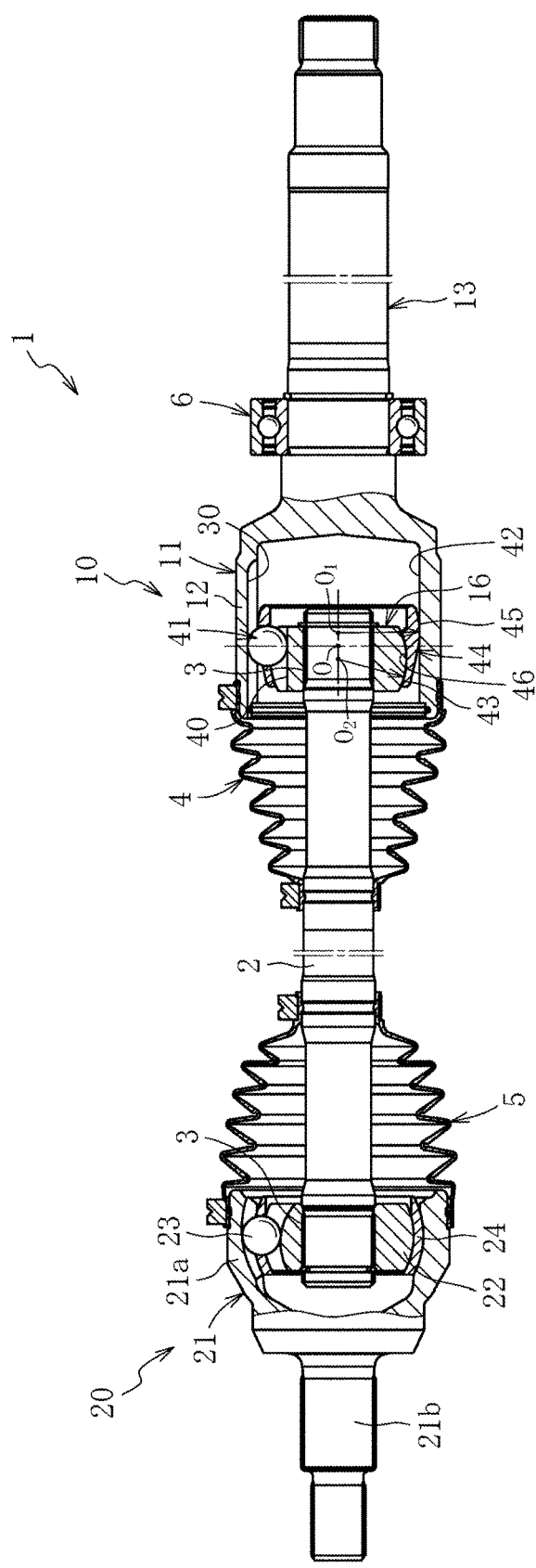
FIG. 1 is a partial sectional front view of a drive shaft including a plunging type constant velocity universal joint with an outer joint member of a long stem type.

FIG. 1 is a view for illustrating the entire structure of a drive shaft 1. The drive shaft 1 mainly comprises a plunging type constant velocity universal joint 10, a fixed type constant velocity universal joint 20, and an intermediate shaft 2 configured to couple both the joints 10 and 20. The plunging type constant velocity universal joint 10 is arranged on a differential side (right side of FIG. 1: hereinafter also referred to as "inboard side"), and the fixed type constant velocity universal joint 20 is arranged on a driving wheel side (left side of FIG. 1: hereinafter also referred to as "outboard side").

The plunging type constant velocity universal joint 10 is a so-called double-offset type constant velocity universal joint (DOJ), and mainly comprises an outer joint member 11, an inner joint member 16, a plurality of balls 41 serving as torque transmitting elements, and a cage 44 configured to retain the balls 41.

The outer joint member 11 comprises a cup section 12 and a long shaft section (hereinafter also referred to as "long stem section") 13 that extends from a bottom of the cup section 12 in an axial direction. The inner joint member 16 is housed in the cup section 12 of the outer joint member 11. Track grooves 30 formed along an inner periphery of the cup section 12 of the outer joint member 11 and track grooves 40 formed along an outer periphery of the inner joint member 16 form pairs, and the balls 41 are arranged between the track grooves 30 and 40 of respective pairs. The cage 44 is interposed between the outer joint member 11 and the inner joint member 16, and is held in contact with a partially cylindrical inner peripheral surface 42 of the outer joint member 11 at a spherical outer peripheral surface 45 and held in contact with a spherical outer peripheral surface 43 of the inner joint member 16 at a spherical inner peripheral surface 46. A curvature center $O_1$ of the spherical outer peripheral surface 45 and a curvature center $O_2$ of the spherical inner peripheral surface 46 of the cage 44 are offset equidistantly from a joint center O toward opposite sides in the axial direction.

An inner ring of a support bearing 6 is fixed to an outer peripheral surface of the long stem section 13, and an outer ring of the support bearing 6 is fixed to a transmission case with a bracket (not shown). As described above, the outer joint member 11 is supported by the support bearing 6 in a freely rotatable manner, and hence vibration of the outer joint member 11 during driving or the like is prevented as much as possible.

The fixed type constant velocity universal joint 20 is a so-called Rzeppa type constant velocity universal joint, and mainly comprises an outer joint member 21, an inner joint member 22, a plurality of balls 23 serving as torque transmitting elements, and a cage 24 configured to retain the balls 23. The outer joint member 21 comprises a bottomed cylindrical cup section 21*a* and a shaft section 21*b* that extends from a bottom of the cup section 21*a* in the axial direction. The inner joint member 22 is housed in the cup section 21*a* of the outer joint member 21. The balls 23 are arranged between the cup section 21*a* of the outer joint member 21 and the inner joint member 22. The cage is interposed between an inner peripheral surface of the cup section 21*a* of the outer joint member 21 and an outer peripheral surface of the inner joint member 22.

Note that, as the fixed type constant velocity universal joint, an undercut-free type constant velocity universal joint may sometimes be used.

The intermediate shaft 2 comprises spline (including serrations; the same applies hereinafter) shafts 3 on both end portions thereof. The spline shaft 3 on the inboard side is inserted to a spline hole of the inner joint member 16 of the plunging type constant velocity universal joint 10. Thus, the intermediate shaft 2 and the inner joint member 16 of the plunging type constant velocity universal joint 10 are coupled to each other to allow torque transmission therebetween. Further, the spline shaft 3 on the outboard side is inserted to a spline hole of the inner joint member 22 of the fixed type constant velocity universal joint 20. Thus, the intermediate shaft 2 and the inner joint member 22 of the fixed type constant velocity universal joint 20 are coupled to each other to allow torque transmission therebetween. Although the example of the solid intermediate shaft 2 is illustrated, a hollow intermediate shaft may also be used.

Grease is sealed inside both the constant velocity universal joints 10 and 20 as a lubricant. To prevent leakage of the grease or entry of a foreign matter, bellows boots 4 and 5 are respectively mounted to a portion between the outer joint member 11 of the plunging type constant velocity universal joint 10 and the intermediate shaft 2, and a portion between the outer joint member 21 of the fixed type constant velocity universal joint 20 and the intermediate shaft 2.

Next, details of the outer joint member 11 are described with reference to FIG. 2*a* to FIG. 2*c*.

The outer joint member 11 comprises the cup section 12 and the long stem section 13. The outer joint member 11 is manufactured by joining the cup member 12*a* and the shaft member 13*a* through butt welding, and manufacturing steps are described later in detail.

The cup section 12 has a bottomed cylindrical shape that is opened at one end, and the inner peripheral surface 42 has the plurality of track grooves 30 that are formed equidistantly in a circumferential direction, thereby forming a partially cylindrical shape. The balls 41 (see FIG. 1) roll on the track grooves 30.

The cup member 12*a* is an integrally-formed product being made of medium carbon steel, e.g., S53C, containing carbon of from 0.40 wt % to 0.60 wt %, and having a cylindrical portion 12*a*1 and a bottom portion 12*a*2. The cylindrical portion 12*a*1 has the track grooves 30 and the inner peripheral surface 42 described above. A boot mounting groove 32 is formed at an outer periphery of the cup member 12*a* on the opening side thereof, whereas a snap ring groove 33 is formed at an inner periphery. The bottom portion 12*a*2 has a shaft section having a solid shaft shape protruding toward the shaft member 13*a* side, that is, a short shaft section 12*a*3, and a joining end surface 50 (FIG. 2*c*) is formed at the short shaft section 12*a*3.

The joining end surface 50 is finished by turning. Herein, a recessed portion 50*b* is formed on a radially inner side of the joining end surface 50, and as a result, the annular joining end surface 50 is formed on a radially outer side of the recessed portion 50*b*. The reference symbol D denotes an inner diameter of the joining end surface 50. The recessed portion 50*b* may be formed during forging, or may be formed by cutting. When the recessed portion 50*b* is formed during forging, the number of steps can be reduced. Further, the joining end surface 50 is formed into an annular shape, and hence time required for turning can be reduced.

The long stem section 13 is a solid shaft that extends from the bottom portion 12*a*2 of the cup section 12 in the axial direction. A bearing mounting surface 14 and a snap ring groove 15 are formed at an outer periphery of the long stem section 13 on the cup member 12*a* side, whereas a spline shaft Sp serving as a torque transmission coupling portion is formed at an end portion on a side opposite to the cup section 12.

The shaft member 13*a* is made of medium carbon steel, e.g., S40C, containing carbon of from 0.30 wt % to 0.55 wt %. A joining end surface 51 (FIG. 2*c*) is formed at an end portion on the cup member 12*a* side. The joining end surface 51 has a recess 52 formed in an inner diameter side. As a result, the joining end surface 51 is formed into an annular surface. The reference symbol E denotes an inner diameter of the joining end surface 51. FIG. 2*a* to FIG. 2*c* and FIG. 5*a* to FIG. 5*c* are illustrations of an example in which the recess 52 is formed during forging and in which the inner diameter portion 53 is formed in the joining end surface 51 by cutting. Thus, it appears as if the recess 52 and the inner diameter portion 53 are formed into a hole having stages. However, the inner diameter portion 53 may be an inner diameter portion of the joining end surface 51, or may be an inner diameter portion of the recess 52. The recess 52 may maintain a forged surface. In that case, the inner diameter portion 53 that can be clearly distinguished from the recess 52 does not appear as illustrated.

The recess 52 has a shallow bottom, that is, is very shallow with respect to an outer diameter of the joining end surface 51. As an example of the depth, a lower limit is approximately 1 mm. That is intended to secure a straight portion having a length in the axial direction necessary to perform ultrasonic flaw detection for defectiveness in dimension in the radial direction (penetration depth) of the welded portion 49. The above-mentioned lower limit is a value in view of the ultrasonic flaw detection. In view of reducing the pre-heating time through reduction of a volume near the joining portion, a corresponding depth of the recess 52 is desired.

In the case of forming the recessed portion during forging, an upper limit of the depth of the recess 52 is approximately a limit value formed through forging (reference)×1.5 mm. Excessively deep recess 52 may cause increase in forging load, degradation of die lifetime, and increase in processing cost. Even in the case of forming through cutting, excessively deep recess 52 may cause longer processing time and poor material yield.

The inner diameter portion 53 of the joining end surface 51, while being dependent on the outer diameter of the shaft member 13*a*, is presupposed to secure a radial width of the welded portion 49 to be formed on the outer diameter side of the recess 52. The term "diameter" of the inner diameter is generally associated with a circular shape. However, a contour of the recess 52 as viewed from a plane perpendicular to the axial line of the shaft member 13a is not limited to have a circular shape, and the shape may be, for example, a polygon or an irregular shape.

Figure 2:
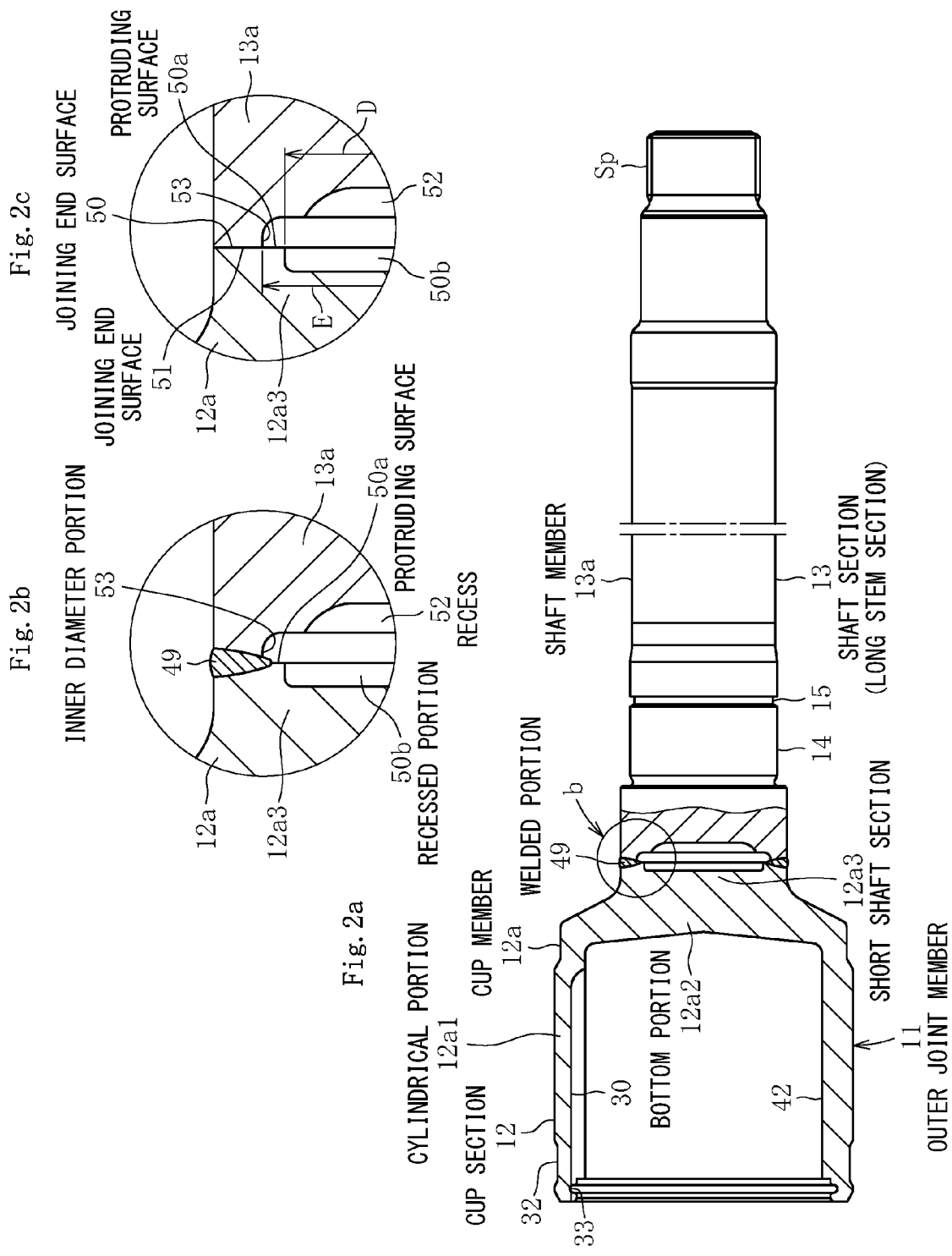

Welding is performed by bringing the joining end surface 50 of the cup member 12a and the joining end surface 51 of the shaft member 13a into abutment against each other and irradiating an electron beam from an outer side of the cup member 12a in the radial direction (FIG. 2a and FIG. 2b). The welded portion 49, as is well known, comprises metal that is molten and solidified during welding, that is, a molten metal and a heat-affected portion in a periphery of the molten metal.

Although detailed description is made later, outer diameters B of the joining end surfaces 50 and 51 (see FIG. 4b and FIG. 5c) are set to equal dimensions for each joint size. However, the outer diameter B of the joining end surface 50 of the cup member 12a and the outer diameter B of the joining end surface 51 of the shaft member 13a need not be set to equal dimensions. In consideration of, for example, a state of the bead, a dimensional difference may be given as appropriate in such a manner that the outer diameter B of the joining end surface 51 is set slightly smaller than the outer diameter B of the joining end surface 50 or the like. The dimensional relationship between the outer diameter B of the joining end surface 50 and the outer diameter B of the joining end surface 51 is the same throughout the Description.

The welded portion 49 is formed on the cup member 12a side with respect to the bearing mounting surface 14 of the shaft member 13a, and hence the bearing mounting surface 14 and the like can be processed in advance before welding so that post-processing after welding can be omitted. Further, in the electron beam welding, burrs are not generated at the welded portion. Thus, also on this point, post-processing for the welded portion can also be omitted, which can reduce manufacturing cost. Still further, total inspection on the welded portion through ultrasonic flaw detection can be performed.

As illustrated in FIG. 2c, an inner diameter D of the joining end surface 50 of the cup member 12a is set smaller than an inner diameter E of the joining end surface 51 of the shaft member 13a. In other words, the recessed portion 50b has a smaller diameter than the recess 52. As a result, the joining end surface 50 of the cup member 12a partially protrudes to a radially inner side with respect to the joining end surface 51 having the inner diameter E. This protruding portion is referred to as a protruding surface 50a. The joining end surfaces 50 and 51 having such a shape are brought into abutment against each other, and the cup member 12a and the shaft member 13a are joined by welding. The protruding surface 50a is formed to be the same for each joint size.

Next, the manufacturing method of the above-mentioned outer joint member is described with reference to FIG. 3 to FIG. 16. Before description of details of each manufacturing step, an overview of manufacturing steps is described.

Figure 3:
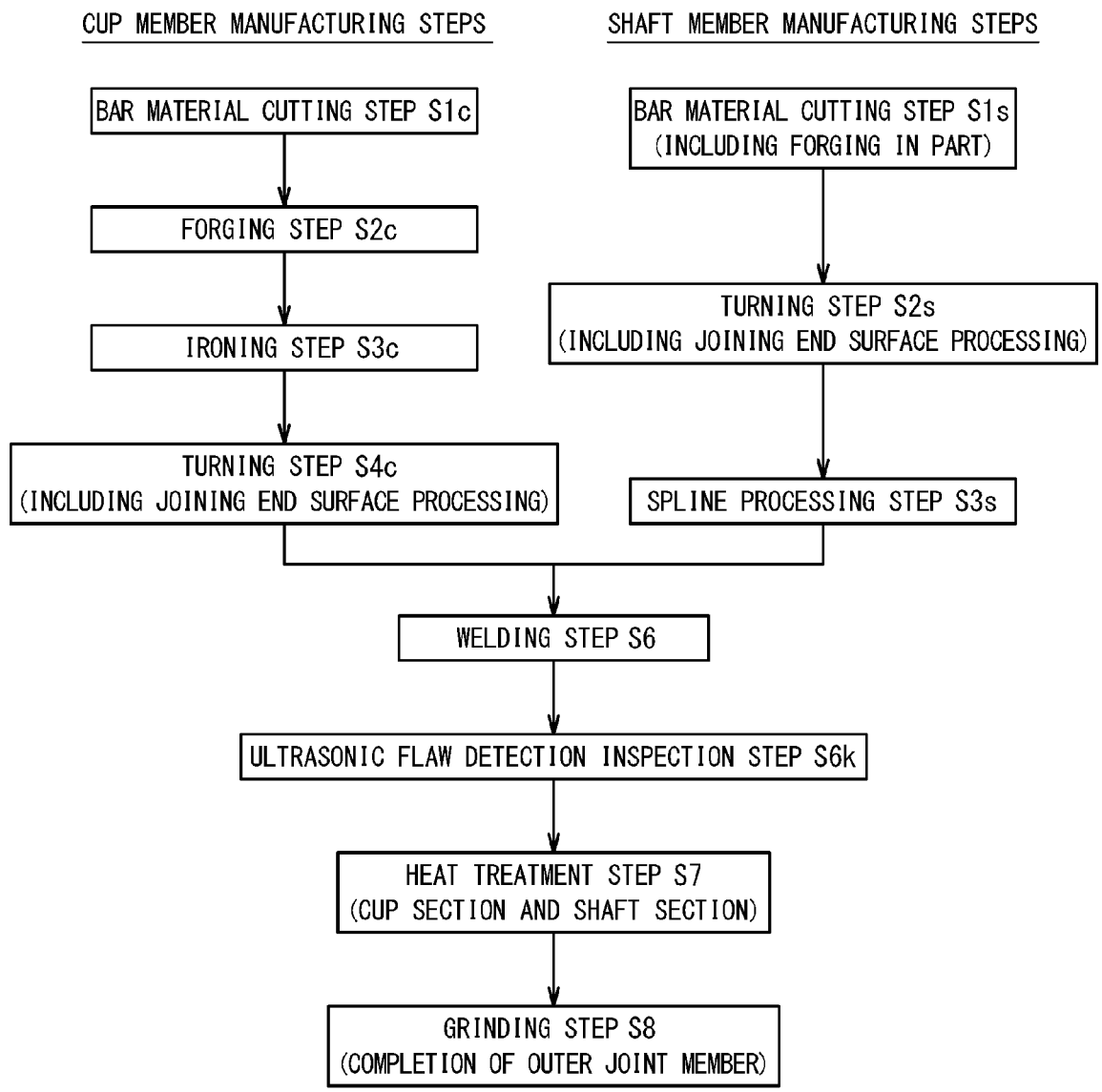
FIG. 3 is a block line diagram for illustrating manufacturing steps for the outer joint member of FIG. 1.

As illustrated in FIG. 3, the cup member 12a is manufactured through manufacturing steps comprising a bar material cutting step S1c, a forging step S2c, an ironing step S3c, and a turning step S4c. Meanwhile, the shaft member 13a is manufactured through manufacturing steps comprising a bar material cutting step S1s, a turning step S2s, and a spline processing step S3s. Intermediate components of the cup member 12a and the shaft member 13a thus manufactured are each assigned with a product number for management. After that, the cup member 12a and the shaft member 13a are subjected to a welding step S6, an ultrasonic flaw detection step S6k, a heat treatment step S7, and a grinding step S8 so that the outer joint member 11 is completed.

An overview of each step is described below. Each step is described as a typical example, and appropriate modification and addition may be made as needed.

First, the manufacturing steps for the cup member 12a are described.

[Bar Material Cutting Step S1c]

A bar material is cut into a predetermined length in accordance with a forging weight, thereby producing a billet.

[Forging Step S2c]

The billet is subjected to forging so as to integrally form the cylindrical portion, the bottom portion, and the projecting portion as a preform of the cup member 12a.

[Ironing Step S3c]

Ironing is performed on the track grooves 30 and the cylindrical surface 42 of the preform, thereby finishing the inner periphery of the cylindrical portion of the cup member 12a.

[Turning Step S4c]

In the preform after ironing, the outer peripheral surface, the boot mounting groove 32, the snap ring groove 33 and the like, and the joining end surface 50 are formed by turning. After the turning step S4c, the cup member 12a in the form of an intermediate component is assigned with a product number for management.

Next, the manufacturing steps for the shaft member 13a are described.

[Bar Material Cutting Step S1s]

A bar material is cut into a predetermined length in accordance with an entire length of the shaft section, thereby producing a billet. After that, the billet is forged into a rough shape by upset forging depending on the shape of the shaft member 13a.

[Turning Step S2s]

The outer peripheral surface of the billet (bearing mounting surface 14, snap ring groove 15, minor diameter of the spline, end surface, and the like) and the joining end surface 51 of the billet at the end portion on the cup member 12a side are formed by turning.

[Spline Processing Step S3s]

The spline shaft is formed by processing splines in the shaft member through rolling after turning. Note that, the method of processing the spline is not limited to the rolling, and press working or the like may be adopted instead as appropriate. After the spline processing, the shaft member 13a in the form of an intermediate component is assigned with a product number for management.

Next, the manufacturing steps in the process of completing the outer joint member 11 from the cup member 12a and the shaft member 13a.

[Welding Step S6]

The joining end surface 50 of the cup member 12a and the joining end surface 51 of the shaft member 13a are brought into abutment against and welded to each other.

[Ultrasonic Flaw Detection Step S6k]

The welded portion 49 between the cup member 12a and the shaft member 13a is inspected by ultrasonic flaw detection.

[Heat Treatment Step S7]

High frequency quenching and tempering are performed as heat treatment on at least the track grooves 30 and the inner peripheral surface 42 of the cup section 12 after welding and a necessary range of the outer periphery of the shaft member 13 after welding. Heat treatment is not performed on the welded portion 49. A hardened layer having a hardness of approximately from 58 HRC to 62 HRC is formed on each of the track grooves 30 and the inner peripheral surface 42 of the cup section 12. Further, a hardened layer having a hardness of approximately from 50 HRC to 62 HRC is formed in a predetermined range of the outer periphery of the shaft section 13.

[Grinding Step S8]

After the heat treatment, the bearing mounting surface 14 of the shaft member 13 and the like are finished by grinding. Thus, the outer joint member 11 is completed.

As described above, the heat treatment step is provided after the welding step, and hence the manufacturing steps are suited to a cup member and a shaft member having such shapes and specifications that the hardness of the heat-treated portion may be affected by temperature rise at the periphery due to heat generated during the welding.

Main constituent features of the above-mentioned method of manufacturing the outer joint member are described more in detail.

Figure 4A:
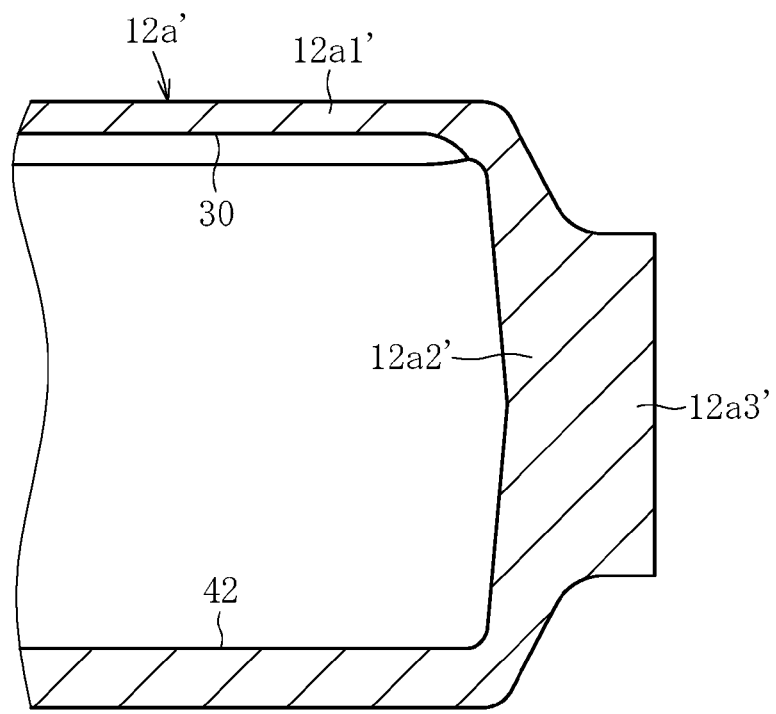
FIG. 4a is a vertical sectional view of a cup member after ironing.
Figure 4B:
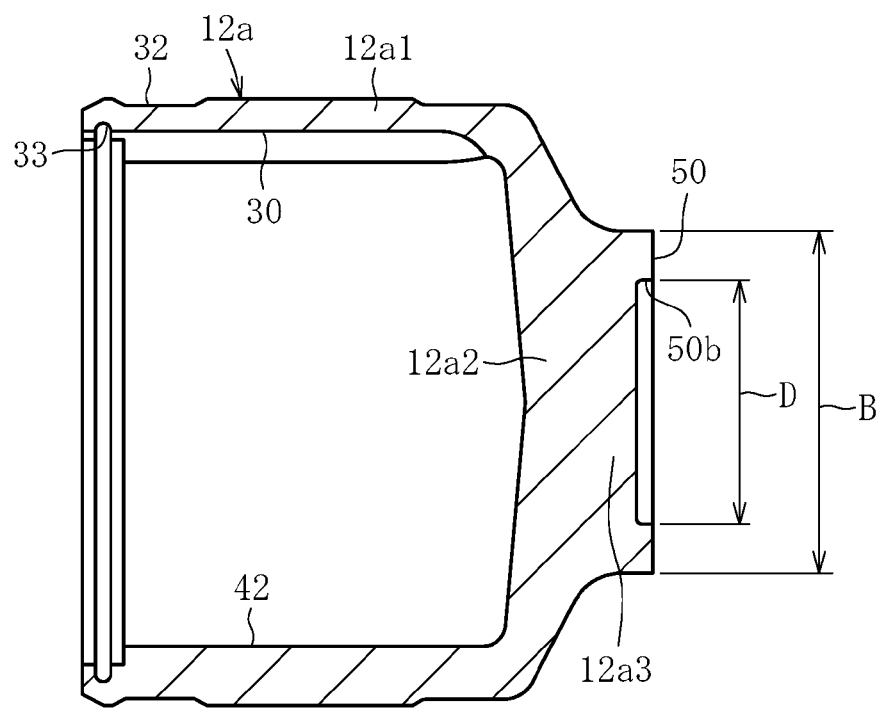
FIG. 4b is a vertical sectional view of the cup member after turning.

FIG. 4a is an illustration of a state after ironing of the cup member 12a. FIG. 4b is an illustration of a state after turning. In a preform 12a' for the cup member 12a, there are integrally formed a cylindrical portion 12a1', a bottom portion 12a2', and a short shaft section 12a3' in the forging step S2c. After that, the track grooves 30 and the cylindrical surface 42 are formed by ironing in the ironing step S3c so that the inner periphery of the cylindrical portion 12a1' is finished as illustrated in FIG. 4a. After that, in the turning step S4c, the outer peripheral surface, the boot mounting groove 32, the snap ring groove 33, and the like of the cup member 12a as well as the joining end surface 50 of the short shaft section 12a3 and the outer diameter B and the inner diameter D of the joining end surface 50 are formed by turning as illustrated in FIG. 4b.

FIG. 5a and FIG. 5b are illustrations of states of the shaft member 13a in the respective processing steps. That is, FIG. 5a is an illustration of a billet 13a" obtained by cutting a bar material. FIG. 5b is an illustration of a preform 13a' obtained by forging the billet 13a" into a rough shape by upset forging. FIG. 5c is an illustration of the shaft member 13a after turning and spline processing.

The billet 13a" illustrated in FIG. 5a is formed in the bar material cutting step S1s. The preform 13a' is formed by increasing, if necessary, the shaft diameter of the billet 13a" in a predetermined range and forming a recess 52 at a joining-side end portion (end portion on the cup member 12a side) by upset forging as illustrated in FIG. 5b. As described above, FIG. 5c is an illustration of an example of forming the recess 52 during forging and forming the inner diameter portion 53 in the opening end portion by turning. However, the recess 52 may maintain a forged surface. In that case, the recess 52 and the inner diameter portion 53 are integrally formed, and hence may not be clearly distinguished from each other.

After that, in the turning step S2s, the outer diameter of the shaft member 13a, the bearing mounting surface 14, the snap ring groove 15, an inner diameter portion 53 (inner diameter E), the joining end surface 51, and the outer diameter B thereof are formed by turning, as illustrated in FIG. 5c. Further, in the spline processing step S3s, the spline shaft Sp is processed at the end portion on the opposite side to the recess 52 by rolling or press forming.

The outer diameter B of the joining end surface 50 of the cup member 12a illustrated in FIG. 4b is set to an equal dimension for one joint size. Further, in the shaft member 13a illustrated in FIG. 5c, which is used for a long stem shaft type, the outer diameter B of the joining end surface 51 located at the end portion on the cup member 12a side is set to an equal dimension to the outer diameter B of the joining end surface 50 of the cup member 12a irrespective of the shaft diameter and the outer peripheral shape. Still further, the joining end surface 51 of the shaft member 13a is located at the position on the cup member 12a side with respect to the bearing mounting surface 14.

Through the setting of dimensions as described above, the outer joint member 11 compatible with various vehicle types can be manufactured in such a manner that, while the cup member 12a is prepared for common use, only the shaft member 13a is manufactured to have a variety of shaft diameters, lengths, and outer peripheral shapes depending on vehicle types, and both the members 12a and 13a are welded to each other. Details of the preparation of the cup member 12a for common use are described later.

Figure 6:
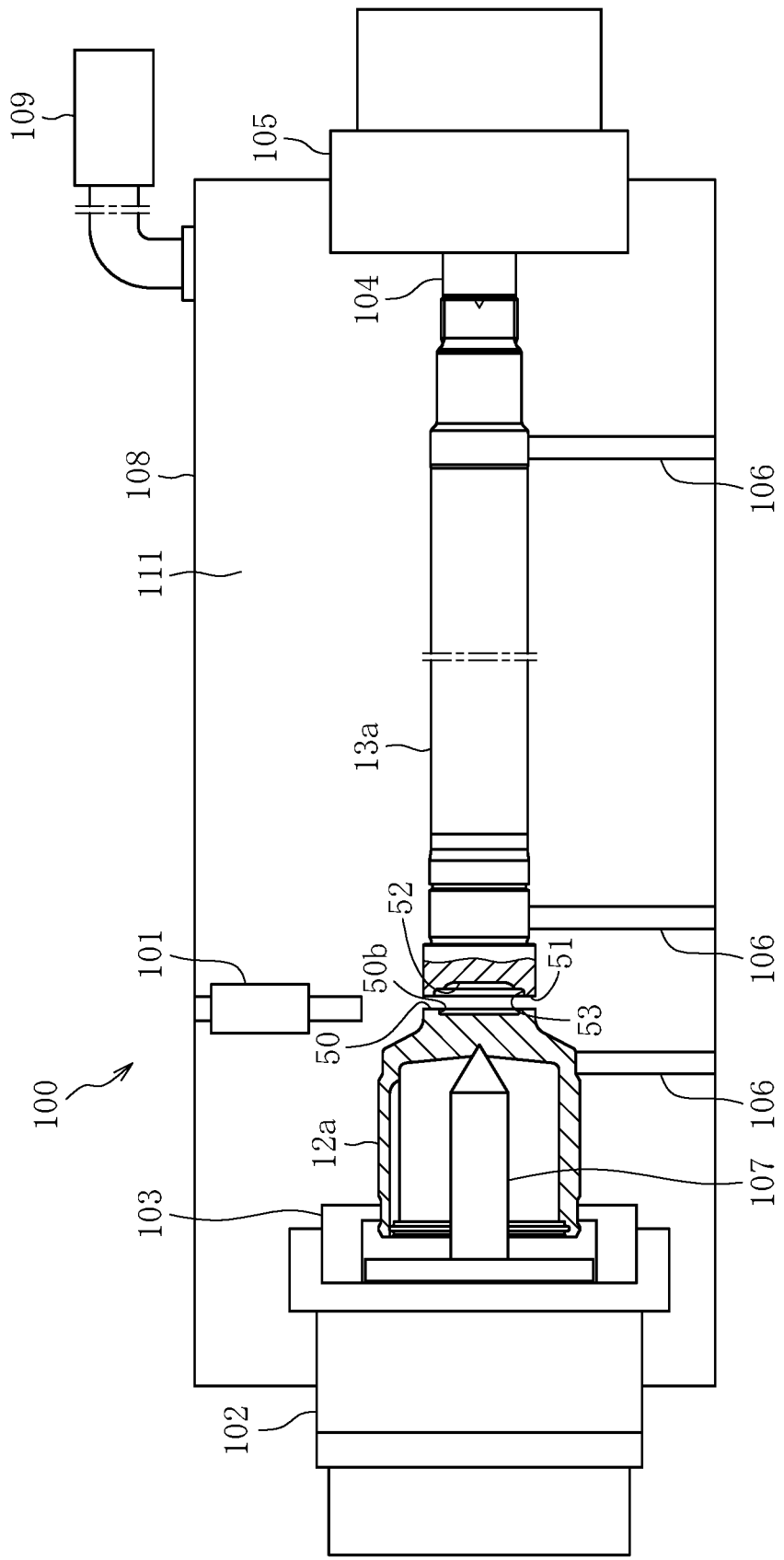
FIG. 6 is a schematic elevation view of a welding apparatus before welding.
Figure 7:
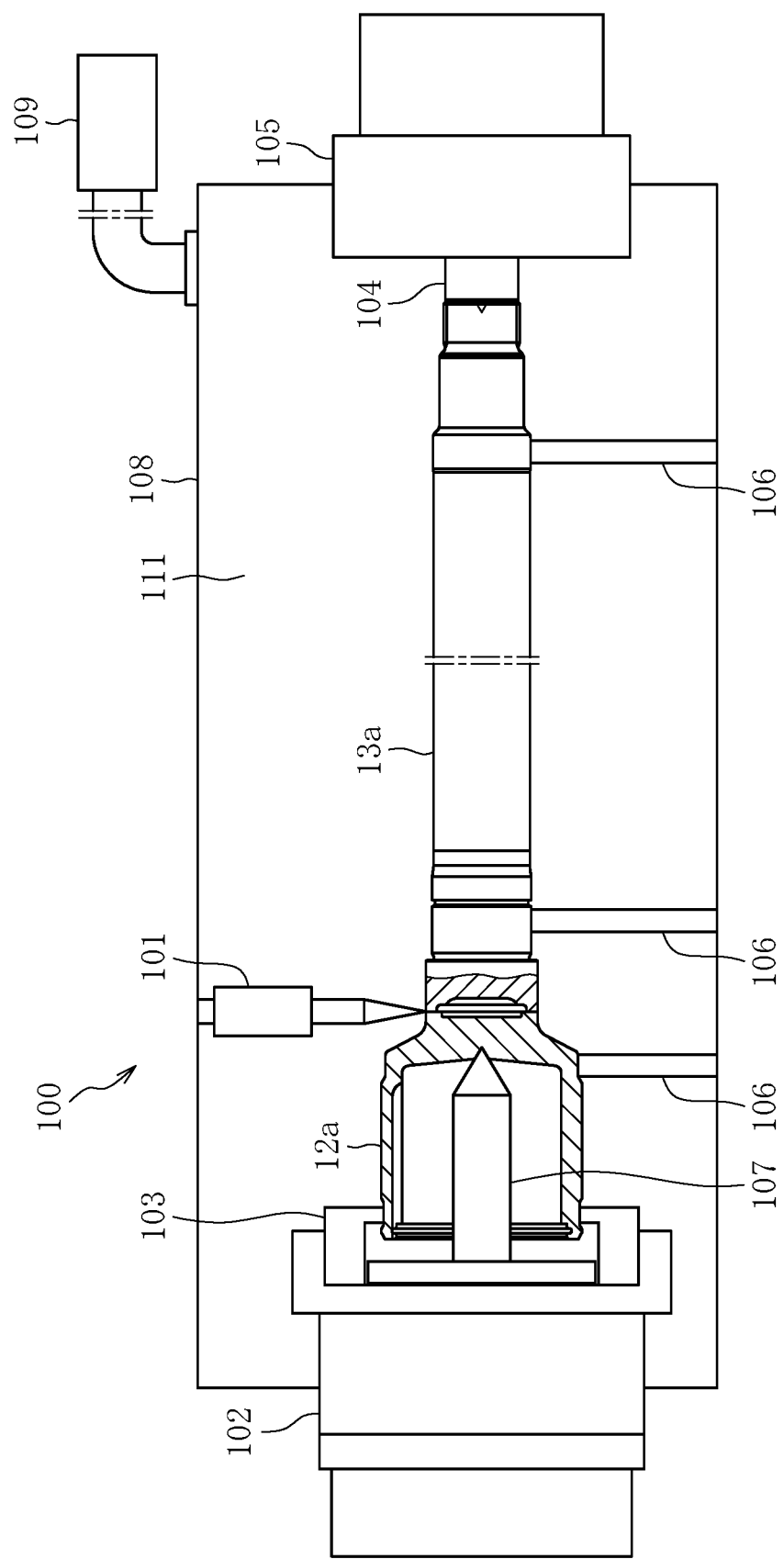
FIG. 7 is a schematic elevation view of the welding apparatus during welding.

Next, welding of the cup member 12a and the shaft member 13a is described with reference to FIG. 6 and FIG. 7. FIG. 6 is a schematic elevation view of a welding apparatus for illustrating a state before welding, and FIG. 7 is a schematic plan view of the welding apparatus for illustrating a state during welding.

As illustrated in FIG. 6, a welding apparatus 100 mainly comprises an electron gun 101, a rotation device 102, a chuck 103, a center 104, a tailstock 105, workpiece supports 106, a center 107, a case 108, and a vacuum pump 109.

The cup member 12a and the shaft member 13a being workpieces are placed on the workpiece supports 106 arranged inside the welding apparatus 100. The chuck 103 and the centering jig 107 arranged at one end of the welding apparatus 100 are coupled to the rotation device 102. The chuck 103 grips the cup member 12a to rotate the cup member 12a by the rotation device 102 under a state in which the center 107 has centered the cup member 12a. The center 104 is integrally mounted to the tailstock 105 arranged at another end of the welding apparatus 100. Both the center 104 and the tailstock 105 are configured to reciprocate in the axial direction (lateral direction of FIG. 6).

A center hole of the shaft member 13a is set on the center 104 so that the shaft member 13a is centered. The vacuum pump 109 is connected to the case 108 of the welding apparatus 100. A "sealed space" herein refers to a space 111 defined by the case 108. The cup member 12a and the shaft member 13a are entirely received in the sealed space 111. The electron gun 101 is arranged at a position corresponding to the joining end surfaces 50 and 51 of the cup member 12a and the shaft member 13a. The electron gun 101 is configured to be approachable to and separable from the workpieces.

The operation of the welding apparatus 100 constructed as described above and the welding method are described below.

The cup member 12a and the shaft member 13a being workpieces are stocked at a place different from the place of the welding apparatus 100. The respective workpieces are taken out by, for example, a robot, are conveyed into the case 108 of the welding apparatus 100 opened to the air as illustrated in FIG. 6, and are set at predetermined positions of the workpiece supports 106. At this time, the center 104 and the tailstock 105 are retreated to the right side of FIG. 6, and hence a gap is formed between the joining end surfaces 50 and 51 of the cup member 12a and the shaft member 13a.

After that, a door (not shown) of the case 108 is closed, and the vacuum pump 109 is activated to reduce the pressure in the sealed space 111 defined in the case 108. Thus, the pressures in the recessed portion 50b of the cup member 12a and the recessed portions 52 and 53 of the shaft member 13a are reduced as well.

When the pressure in the sealed space 111 is reduced to a predetermined pressure, the center 104 and the tailstock 105 are advanced to the left side as illustrated in FIG. 7 to eliminate the gap between the joining end surfaces 50 and 51 of the cup member 12a and the shaft member 13a. Thus, the cup member 12a is centered by the center 107 and fixed by the chuck 103, whereas the shaft member 13a is centered and supported by the center 104. After that, the workpiece supports 106 are moved away from the workpieces (12a and 13a). At this time, the distance between the workpiece supports 106 and the workpieces (12a and 13a) may be infinitesimal, and hence illustration of this distance is omitted from FIG. 7. As a matter of course, the welding apparatus 100 may have such a structure that the workpiece supports 106 are retreated downward greatly.

Although illustration is omitted, the electron gun 101 is then caused to approach the workpieces (12a and 13a) up to a predetermined position, and the workpieces (12a and 13a) are rotated to start pre-heating. As a pre-heating condition, unlike the welding condition, the temperature is set lower than the welding temperature by, for example, radiating an electron beam under a state in which the electron beam is larger than the beam size during welding. The cooling rate after welding is reduced by pre-heating, thereby being capable of preventing a quenching crack. When a predetermined pre-heating time has elapsed, the electron gun 101 is retreated to a predetermined position, and radiates the electron beam from the outer side of the workpieces (12a and 13a) in the radial direction to start welding. When the welding is finished, the electron gun 101 is retreated, and the rotation of the workpieces (12a and 13a) is stopped.

Although illustration is omitted, the sealed space 111 is then opened to the air. Then, the center 104 and the tailstock 105 are retreated to the right side in the drawing sheet and the chuck 103 is opened under a state in which the workpiece supports 106 are raised to support the workpieces. After that, for example, the robot grips the workpieces (12a and 13a), takes the workpieces out of the welding apparatus 100, and places the workpieces into alignment on a cooling stocker. In this embodiment, the cup member 12a and the shaft member 13a are entirely received in the sealed space 111, and hence the configuration of the sealed space 111 defined in the case 108 can be simplified.

Specific conditions for welding are exemplified below.

The cup member 12a having a carbon content of from 0.4% to 0.6% and the shaft member 13a having a carbon content of 0.3% to 0.55% were used and welded to each other in the welding apparatus 100 under the condition that the pressure in the sealed space 111 defined in the case 108 was set to 6.7 Pa or less. In order to prevent rapid cooling after the welding to suppress excessive increase in hardness of the welded portion, a periphery including the joining end surfaces 50 and 51 of the cup member 12a and the shaft member 13a were soaked by pre-heating with the electron beam to have a temperature of from 300° C. to 650° C., and then electron beam welding was performed. As a result, the pre-heating time was able to be reduced to approximately one-half or less as compared to the case where the recess is not formed in the inner diameter side of the joining end surface, and a favorable welded portion satisfying the required strength was able to be obtained.

As a result, a welded portion having a projecting height from the welded surface (0.5 mm or less), which imposed no adverse effect on a product function, was obtained. Further, through the soaking by pre-heating, the hardness of the welded portion after completion of the welding was able to be kept within a range of from 200 HV to 500 HV, thereby being capable of attaining high welding strength and stable welding state and quality. Still further, welding was performed under the condition that the pressure in the sealed space 111 defined in the case 108 of the welding apparatus 100 was set to an atmospheric pressure or less, thereby being capable of suppressing the change in pressure in a hollow cavity portion during the welding. As a result, the blowing of a molten material and the entry of the molten material toward the radially inner side were able to be prevented. For example, a ventilation hole communicating with an inside of the cup member 12a and with the recess 52 may be formed, and the space inside the cup member 12a may be drawn to vacuum to the pressure of 1.3 Pa, and thereafter the joining surfaces may be brought into abutment against each other for welding.

Next, the ultrasonic flaw detection step is described with reference to FIG. 8 to FIG. 13.

Figure 8:
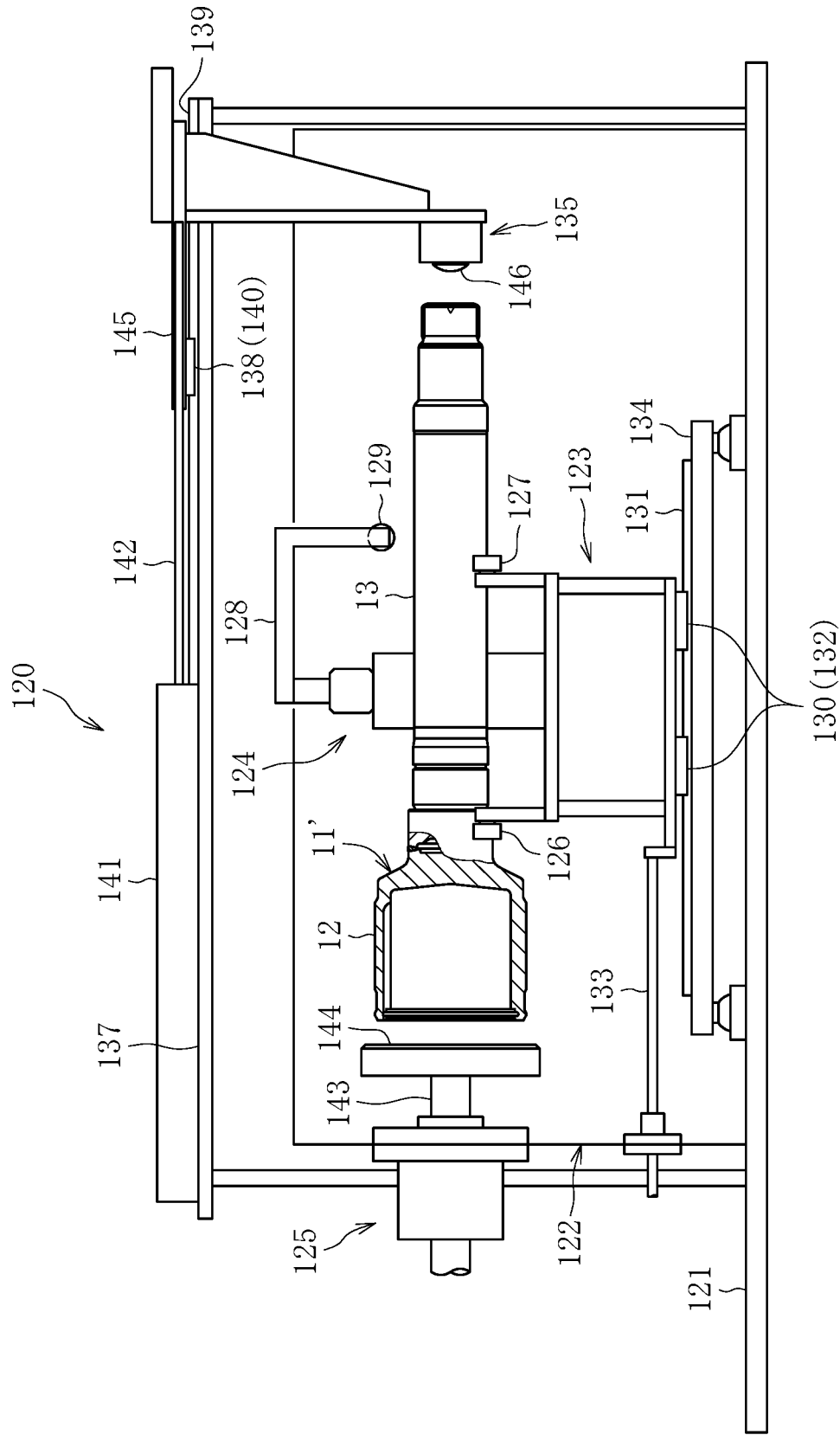
FIG. 8 is a schematic elevation view of an ultrasonic flaw-detection apparatus.
Figure 9:
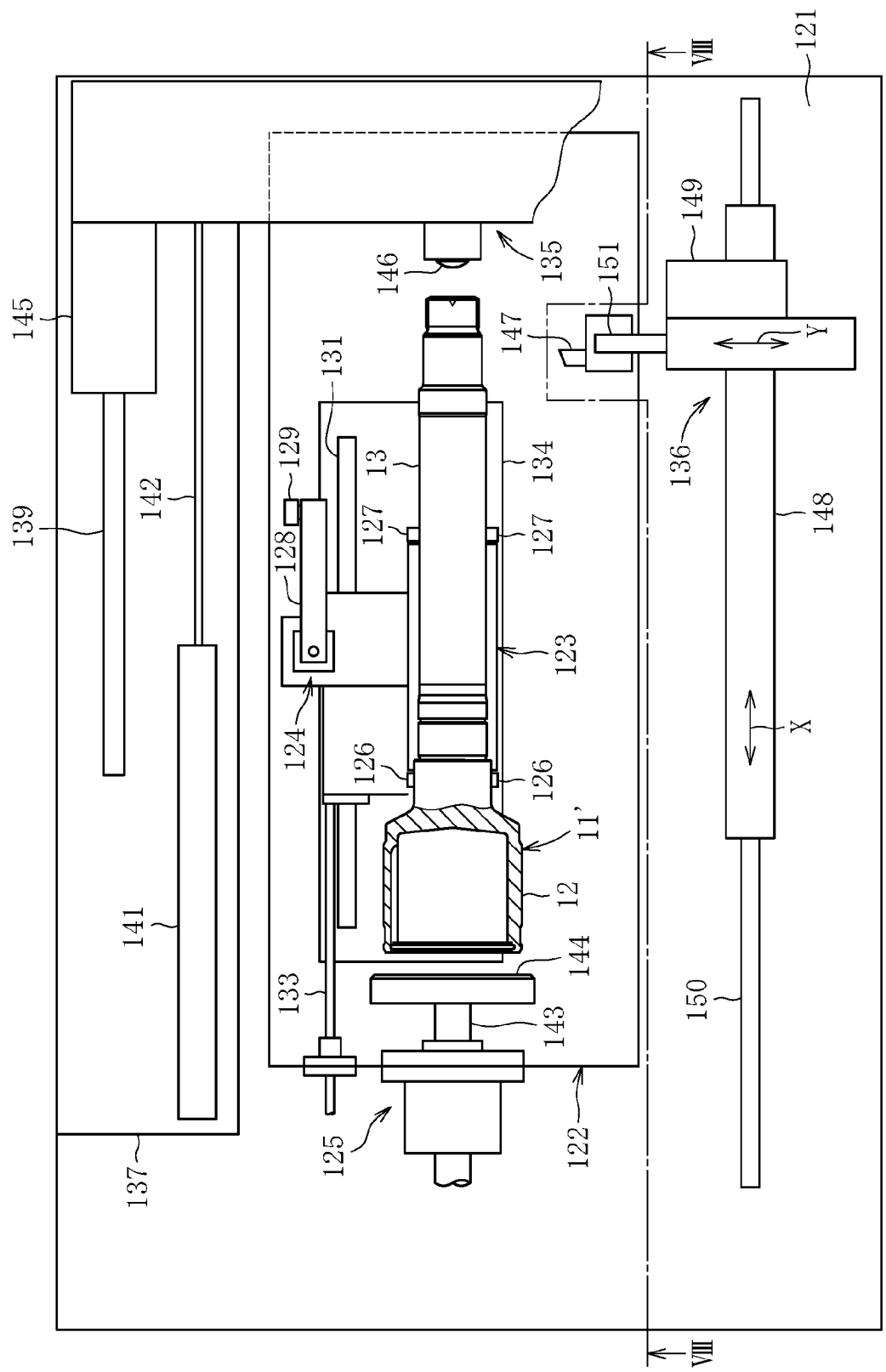
FIG. 9 is a schematic plan view of the ultrasonic flaw-detection apparatus.
Figure 10:
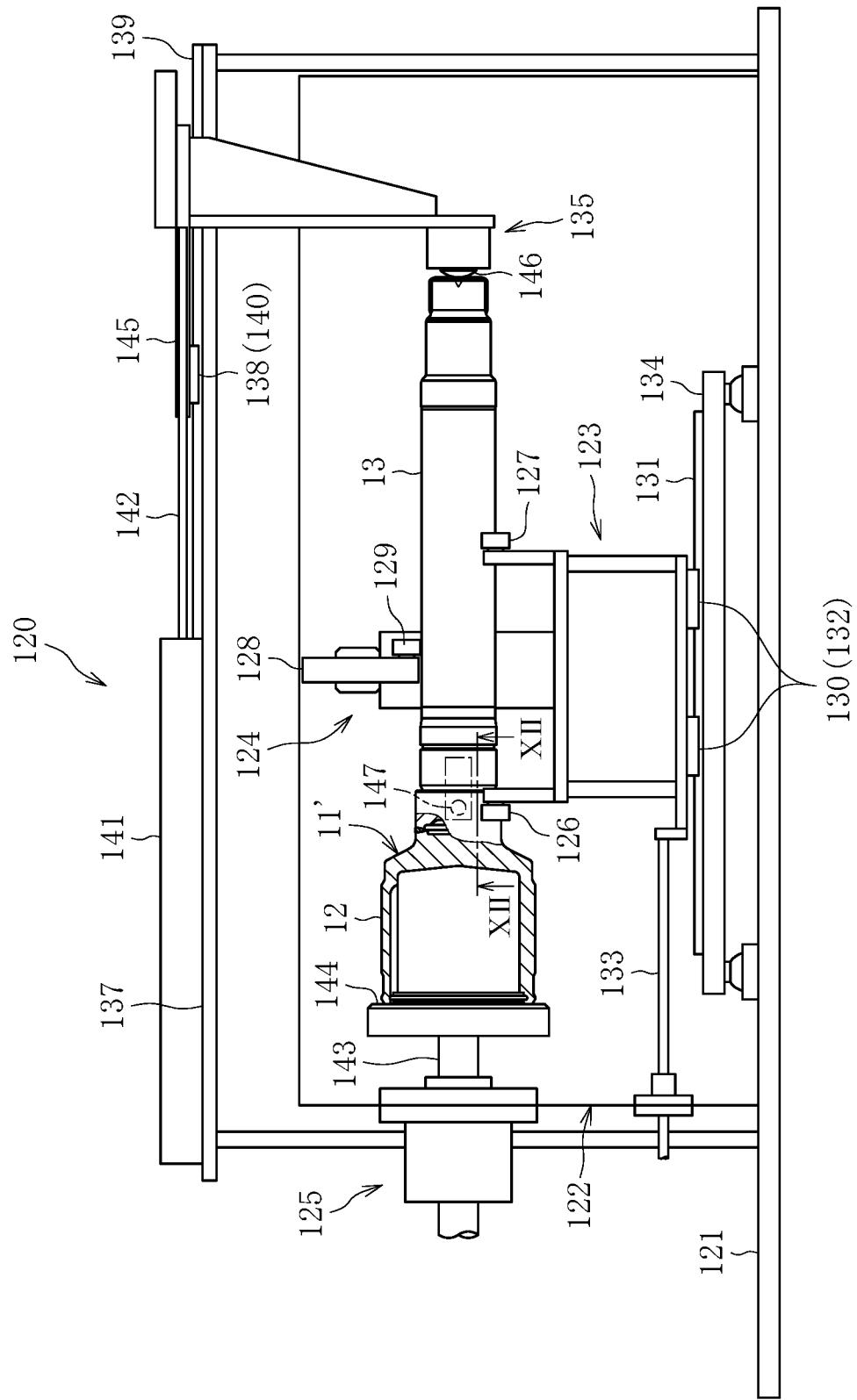
FIG. 10 is a schematic elevation view of the ultrasonic flaw-detection apparatus.
Figure 11:
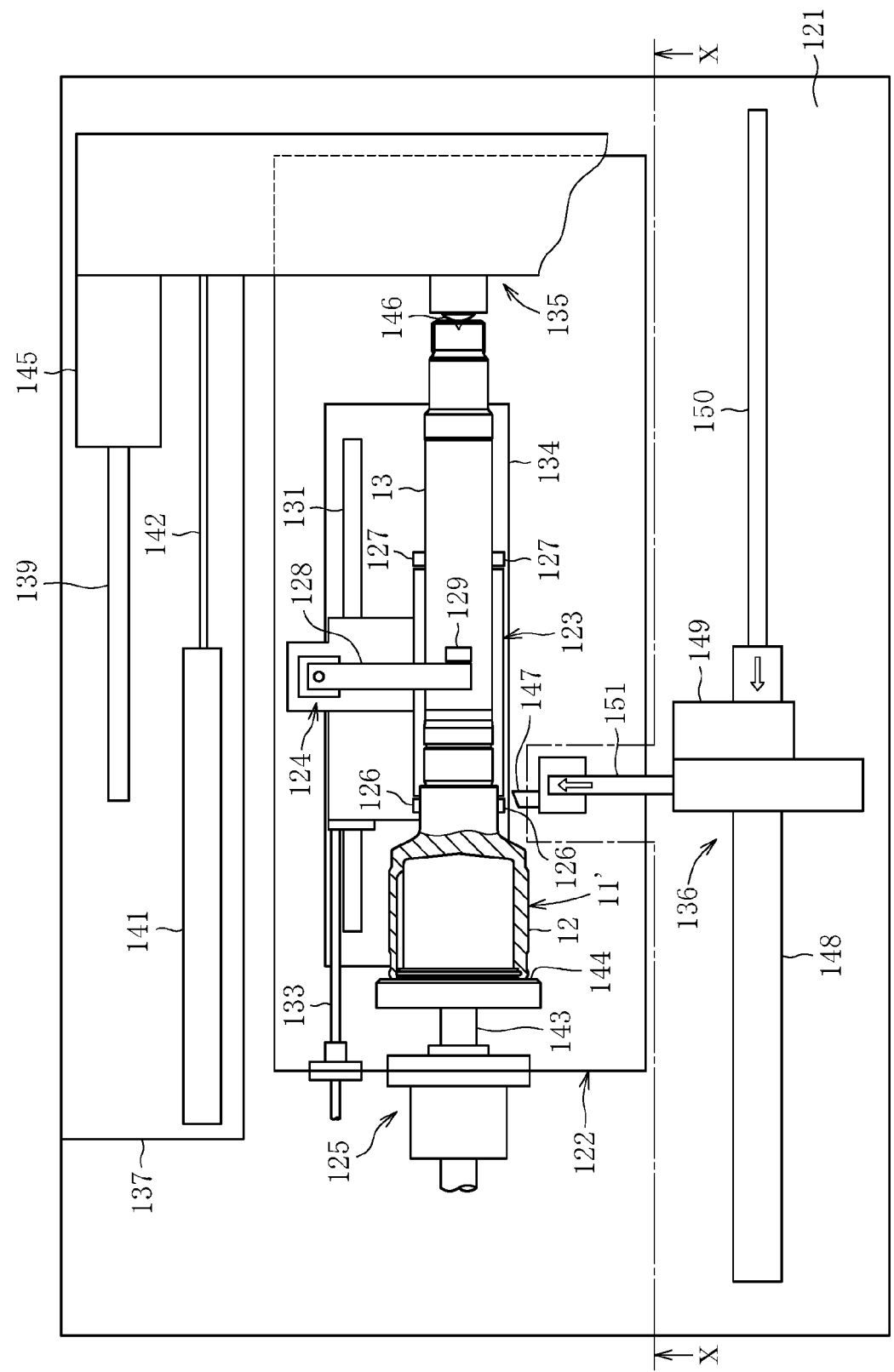
FIG. 11 is a schematic plan view of the ultrasonic flaw-detection apparatus.

Herein, FIG. 8 and FIG. 9 are a front view and a plan view, respectively, of an ultrasonic flaw-detection apparatus having a welded outer joint member mounted thereto. FIG. 8 corresponds to an illustration as viewed from the direction of the arrow VIII-VIII of FIG. 9. FIG. 10 and FIG. 11 are a front view and a plan view, respectively, of the ultrasonic flaw-detection apparatus during the ultrasonic flaw detection. FIG. 10 corresponds to an illustration as viewed from the direction of the arrow X-X of FIG. 11.

As illustrated in FIG. 8 and FIG. 9, an ultrasonic flaw-detection apparatus 120 mainly comprises a base 121, a water bath 122, a workpiece support 123, a workpiece holding member 124, a rotary drive device 125, a pressing device 135, and a drive positioning device 136 (see FIG. 9). The water bath 122 is mounted at the center of the base 121. The rotary drive device 125 is configured to rotate an intermediate product 11' (hereinafter also referred to as "workpiece 11'") of the outer joint member 11. The pressing device 135 is configured to press an axial end of the workpiece 11'. The drive positioning device 136 is configured to drive and position a probe.

The workpiece support 123 comprises support rollers 126 and 127 configured to allow the workpiece 11' to be placed thereon in a freely rotatable manner. The support rollers 126 are arranged at a position close to the welded portion. The support rollers 127 are arranged near a center portion of the shaft section 13. As is apparent from FIG. 9, the support rollers 126 and 127 are constructed by pairs of rollers provided on both sides in the axial line of the shaft section 13 so that the shaft section 13 of the workpiece 11' can be stably supported. The support rollers 126 and 127 are capable of adjusting the placement position of the workpiece 11' in the axial direction (lateral direction of FIG. 8) and the radial direction (vertical direction of FIG. 8) in consideration of a joint size, dimensions, and weight balance of the workpiece 11'.

Further, the workpiece holding member 124 is mounted to the workpiece support 123 at a position displaced in a plane of FIG. 9 from an axial line of the workpiece 11'. The workpiece holding member 124 comprises a lever 128, and a workpiece holding roller 129 is arranged at an end portion of the lever 128. The lever 128 is pivotable in the plane of FIG. 9, and is movable in the vertical direction of FIG. 8.

The workpiece support 123 is mounted to a support 134 through intermediation of a linear-motion bearing 130 comprising rails 131 and linear guides 132, and is movable in the axial direction (lateral direction of FIG. 8 and FIG. 9). The support 134 is mounted to the base 121. The workpiece support 123 can be driven to be positioned at a desired position by an actuator (not shown) arranged on an outside of the water bath 122 through intermediation of a rod 133 coupled to an end portion (left end portion of FIG. 8 and FIG. 9).

The rotary drive device 125 comprises a rotary shaft 143 having a rotary disc 144 mounted thereto, and this rotary shaft 143 is driven to rotate by a motor (not shown) arranged on the outside of the water bath 122.

A mounting base 137 is arranged on an upper side of the ultrasonic flaw-detection apparatus 120. A base plate 145 for the pressing device 135 is mounted to the mounting base 137 through intermediation of a linear-motion bearing 138 comprising a rail 139 and a linear guide 140 so that the base plate 145 of the pressing device 135 is movable in the axial direction (lateral direction of FIG. 8 and FIG. 9). A rod 142 of a pneumatic cylinder 141 is coupled to an end portion of the base plate 145 so that the base plate 145 is driven, that is, axially moved by the pneumatic cylinder 141. The pressing device 135 is held in abutment against the axial end of the shaft section 13 of the workpiece 11' through a free bearing 146.

As viewed in the plane of FIG. 9, the drive device 136 for a probe is arranged at a position displaced in the axial line of the workpiece 11'. This drive device 136 comprises actuators for the X-axis direction and the Y-axis direction so that a probe 147 is driven to be positioned in the X-axis direction and the Y-axis direction. An actuator 148 for the X-axis direction and an actuator 149 for the Y-axis direction are each an electric ball-screw type (ROBO cylinder), which is capable of performing positioning with high accuracy. The reference symbol 150 denotes a rail for a linear-motion bearing. The drive device 136 is arranged on the outside of the water bath 122, and the probe 147 and a holder 151 therefor are arranged in the water bath 122.

Next, the operation of the ultrasonic flaw-detection apparatus 120 having the above-mentioned configuration and the ultrasonic flaw detection step S6k are described below.

First, the workpiece 11' after welding is placed on the workpiece support 123 by a loader (not shown) (see FIG. 8 and FIG. 9). At this time, the workpiece support 123 is located at an appropriate interval from the rotary drive device 125 in the axial direction of the workpiece 11', and the workpiece holding member 124 raises and pivots the lever 128 thereof so as to be substantially parallel to the axial line of the workpiece 11'. Further, the pressing device 135 and the drive device 136 for a probe wait at retreated positions.

After that, the lever 128 of the work piece holding member 124 is pivoted so as to be substantially perpendicular to the axial line of the workpiece 11', and then lowered to hold the workpiece 11' from above (see FIG. 10). Then, water is supplied to the water bath 122. As described above, the ultrasonic flaw-detection apparatus 120 has the configuration of performing flaw detection under water, and hence ultrasonic waves are satisfactorily propagated. Thus, inspection can be performed with high accuracy.

Next, as illustrated in FIG. 10 and FIG. 11, the pneumatic cylinder 141 is driven to cause the pressing device 135 to be advanced and pressed against the axial end of the workpiece 11', thereby pressing the opening rim of the cup section 12 of the workpiece 11' against the rotary disc 144 of the rotary drive device 125. In conjunction with the advance of the pressing device 135, the workpiece support 123 is also moved toward the rotary drive device 125. Thus, the workpiece 11' is positioned in the axial direction and the radial direction. In this state, the motor (not shown) of the rotary drive device 125 is activated, thereby rotating the workpiece 11'.

As illustrated in FIG. 11 with the outlined arrow, the drive device 136 is moved in the X-axis direction, and then moved in the Y-axis direction, thereby positioning the probe 147 at a flaw detection position. The probe 147 in this state is indicated by the broken line in FIG. 10. Then, the ultrasonic flaw detection is performed. After the completion of the ultrasonic flaw detection, water is drained from the water bath 122, and the workpiece 11' is delivered from the ultrasonic flaw-detection apparatus 120 by the loader (not shown). In such a manner, the ultrasonic flaw detection is sequentially repeated on the workpiece 11'.

In order to reduce the cycle time of the ultrasonic flaw detection, it is desired that time-consuming supply and drainage of water be performed simultaneously with operations of the devices and the members, or at other timings in accordance therewith. Further, some of the operations of the devices and the members may be performed simultaneously with each other or in different orders as appropriate.

Figure 12A:
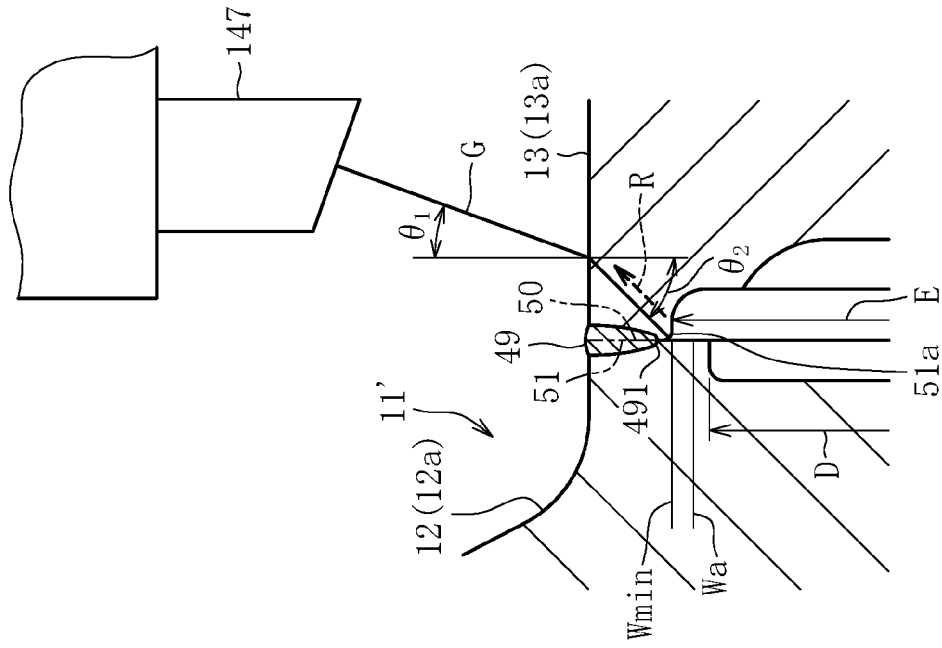
FIG. 12a is a partial enlarged sectional view taken along the line XII-XII of FIG. 10 in a case of a non-defective welded product.
Figure 12B:
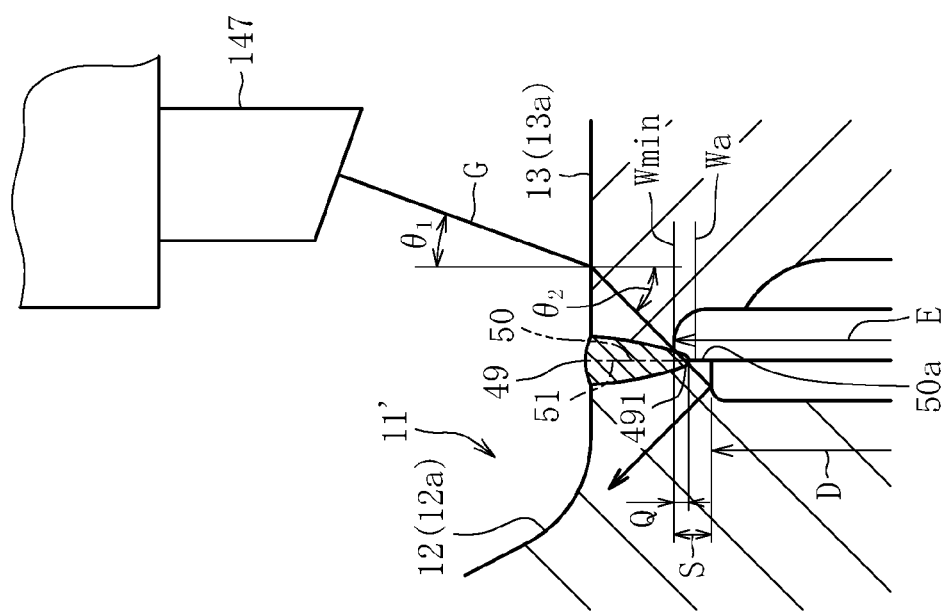
FIG. 12b is a partial enlarged sectional view taken along the line XII-XII of FIG. 10 in a case of a defective welded product.
Figure 13:
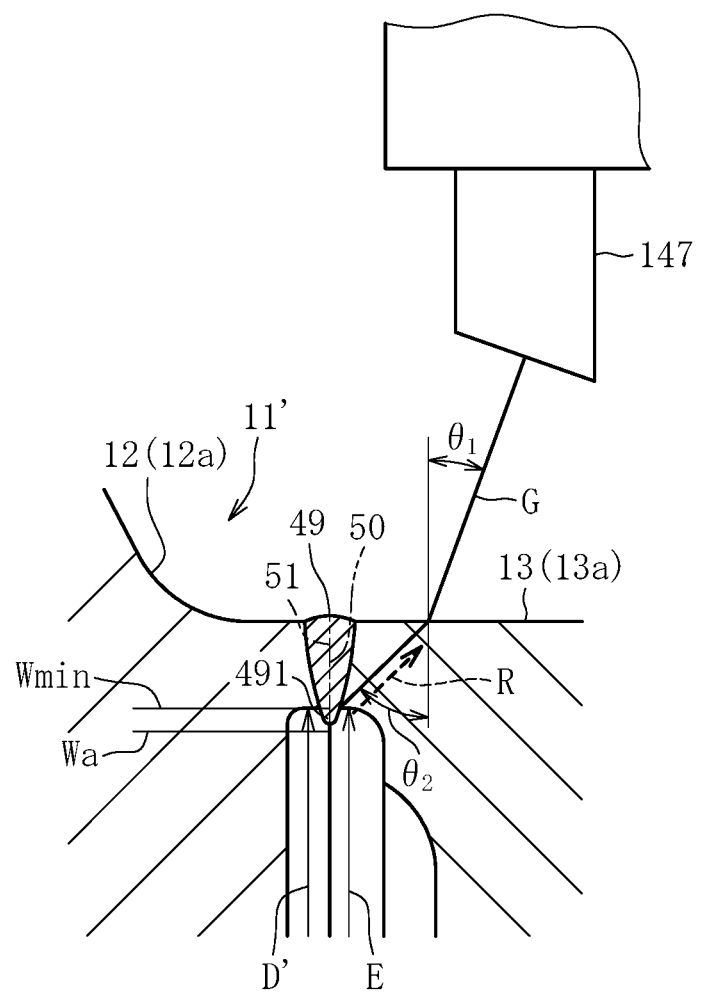
FIG. 13 is a partial enlarged sectional view, which is similar to FIG. 12a and FIG. 12b, for illustrating findings in the course of development.

Details of the ultrasonic flaw detection are described with reference to FIG. 12a, FIG. 12b, and FIG. 13. All of FIG. 12a, FIG. 12b, and FIG. 13 are views as viewed from the arrow XII-XII of FIG. 10. FIG. 12a is an illustration of a non-defective welded product. FIG. 12b is an illustration of a defective welded product. FIG. 13 is a view for illustrating findings in the course of development.

The probe 147 is positioned at a flaw detection position away from the welded portion 49 by a predetermined distance. The flaw detection position is preset for each joint size. A transmission pulse G from the probe 147 is caused to obliquely enter from a surface of the workpiece 11'. A reflected echo having been received is displayed as waveforms, and the waveforms maybe observed to determine a presence or absence of defectiveness (angle beam flaw detection method). The reference symbol $\theta 1$ denotes an incident angle, and the reference symbol $\theta 2$ denotes a refraction angle. In the case of the embodiment, the incident angle $\theta 1$ is about 20°, and the refraction angle $\theta 2$ is about 45°.

Herein, a presence or absence of the penetration defectiveness is mainly detected through detection of a position of a back bead. That is, workpieces having a penetration depth equal to or larger than a determination reference Wmin to reach a radially inner side are determined as non-defective welded products, and workpieces having a penetration depth smaller than the determination reference Wmin to terminate on a radially outer side are determined as defective welded products. In the illustrated example, the inner diameter portion 53 of the recess 52 formed in the joining end surface 51 is matched with the determination reference Wmin. The reference symbol E denotes an inner diameter of (the inner diameter portion 53 of) the recess 52, and also denotes an inner diameter of the joining end surface 51. The reference symbol Wa denotes a target penetration depth. Incidentally, after the welding, the welded portion 49 is formed on the radially outer side of the recess 52. As a result, a closed cavity is formed on the radially inner side of the welded portion 49. Thus, a back bead 491 cannot be visually confirmed from outside.

During the ultrasonic flaw detection, the workpiece 11' is driven by the rotary drive device 125 to rotate. The probe 147 positioned at the flaw detection position away from the welded portion 49 by the predetermined distance collects data of the entire periphery of the workpiece 11'. Specifically, in consideration of tolerance for displacement of the welding position, at the above-mentioned flaw detection position, first, data of a single rotation (360°) of the workpiece 11' is collected. Then, the probe 147 is sequentially shifted in the axial direction at a minute pitch (for example, 0.5 mm) to collect data of a plurality of rotations (for example, five rotations). Based on those pieces of data, non-defective/defective determination is made. A threshold of a reflected echo to be used in the non-defective/defective determination is determined based on a welding pattern corresponding to the determination reference Wmin.

As already described above, in the joining end surface 50 of the cup member 12a, there is formed the protruding surface 50a which protrudes toward the radially inner side with respect to the inner diameter E of the joining end surface 51 of the shaft member 13a. With the above-mentioned shape, the following advantages in the ultrasonic flaw detection can be obtained.

For easy understanding of the above-mentioned advantages, description is preferentially made of findings in the course of development, that is, the case in which an inner diameter D' of the joining end surface 50 of the cup member 12a is set to an equal dimension to the inner diameter E of the joining end surface 51 of the shaft member 13a as illustrated in FIG. 13. In this case, the penetration depth is equal to or larger than the determination reference Wmin to reach the radially inner side, and hence the workpiece is to be determined as a non-defective welded product. However, when the transmission pulse G enters from the probe 147, due to the boundary surface of the back bead 491, which is perpendicular to the transmission pulse G, a reflected echo R reflected by this boundary surface is received by the probe 147. Although reflected echoes from the back bead 491 are scattered, the reflected echo R has a large echo height exceeding the threshold of the reflected echo for the non-defective/defective determination. Thus, determination that the welded product is defective is made. For this reason, it was proved that the determination as to whether the welded product was non-defective or defective was difficult.

Thus, in the embodiment, a measure is taken by forming the protruding surface 50a, which protrudes toward the radially inner side with respect to the inner diameter E of the joining end surface 51 of the shaft member 13a, in the joining end surface 50 of the cup member 12a.

As illustrated in FIG. 12a, the non-defective welded product has sufficient penetration. In this case, the transmission pulse G from the probe 147 enters the cup section 12 through the back bead 491 having reached the radially inner side beyond the determination reference Wmin, and travels straight as it is. Alternatively, the transmission pulse G travels to the cup section 12 side by being reflected due to the inner diameter D of the cup section 12. Therefore, the probe 147 does not receive a reflected echo. That is, even when the transmission pulse G enters the back bead 491, the boundary surface of the back bead 491, which is perpendicular to the transmission pulse G, does not exist. Therefore, although a slightly-scattered reflected echo is generated, the reflected echo which may cause the detection error is not generated. Thus, the echo height of the reflected echo received by the probe 147 is equal to or less than the threshold, and hence determination that the welded product is non-defective is made.

As described above, when the protruding surface 50a is formed on the joining end surface 50 of the cup member 12a, the echo height of the reflected echo becomes lower. Thus, the accuracy in the inspection can be enhanced.

In the case of the defective welded product, as illustrated in FIG. 12b, a distal end of the bead 491 does not reach the determination reference Wmin due to the defective penetration. Thus, the transmission pulse G is reflected by the joining end surface 51 and a chamfered portion 51a, and the scattered reflected echo R is received by the probe 147. The reflected echo R exceeds the threshold of the reflected echo for the non-defective/defective determination, and hence determination that the welded product is defective is made.

As described above, the protruding surface 50a is formed on the joining end surface 50, and hence the echo heights of the reflected echoes can be clearly discriminated from each other. Thus, the determination as to whether the welded product is non-defective or defective can be made with high accuracy.

Dimensions of the protruding surface 50a are set so that a relationship of S≥Q is established, where S [S=(E−D)/2] is a width of the protruding surface 50a in a radial direction, and where Q is a height of the back bead 491 from the inner diameter E of the joining end surface 51 as illustrated in FIG. 12a. When this relationship is satisfied, the heights of the reflected echoes can be clearly discriminated from each other. Thus, the determination as to whether the welded product is non-defective or defective can be made with high accuracy. As long as the relationship of S≥Q is maintained, the dimensions of the protruding surface 50a may be set as appropriate. The inner diameter E of the joining end surface 51 is also an inner diameter (of the inner diameter portion 53) of the recess 52.

In the ultrasonic flaw-detection apparatus 120, the operation of loading the workpiece 11', the supply and drainage of water, the ultrasonic flaw detection, and the operation of unloading the workpiece can be performed in conjunction with each other, and the ultrasonic flaw detection can be automated. Thus, accuracy, operability, and efficiency in the inspection can be enhanced, which is suited to the inspection on the welded portion of the outer joint member of the constant velocity universal joint being a mass-produced product.

Further, in the ultrasonic flaw detection, with the base configuration in which the outer diameter B of the joining end surface 50 of the cup member 12a is set to an equal dimension for each joint size, setup and replacement operations with respect to the outer joint members 11 having the different product numbers are reduced. Thus, the efficiency in the inspection can be further enhanced.

Still further, flaw detection is performed underwater, and hence ultrasonic waves are satisfactorily propagated. Thus, inspection can be performed with much higher accuracy. In addition, through employment of the shape of the welded portion, in which the protruding surface 50a is formed on the joining end surface 50, the echo heights of the reflected echoes can clearly be discriminated from each other. Thus, the determination as to whether the welded product is non-defective or defective can be made with high accuracy.

Next, standardization of a product type of the cup member is additionally described while exemplifying a shaft member having a product number different from that of the above-mentioned shaft member 13a of the long stem type illustrated in FIG. 5c.

Figure 14:
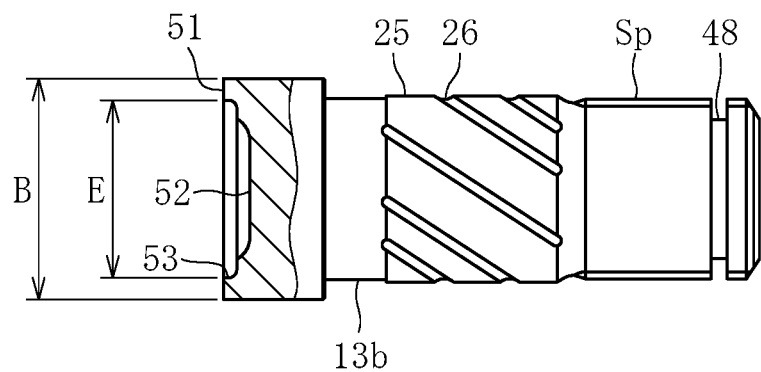
FIG. 14 is a partial sectional front view for illustrating a shaft member assigned with a different product number.
Figure 15:
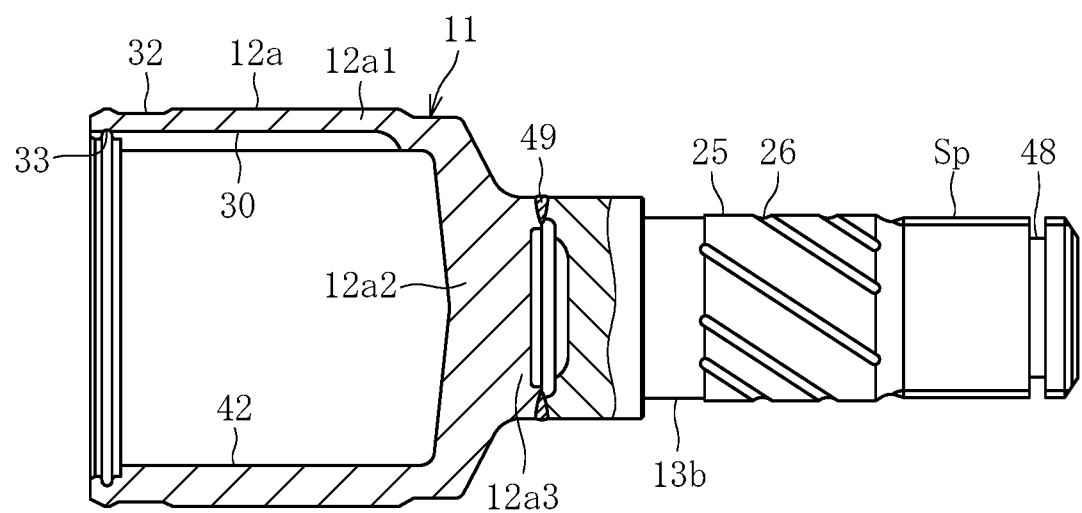
FIG. 15 is a partial sectional front view of an outer joint member that is manufactured using the shaft member of FIG. 14.

A shaft member 13b illustrated in FIG. 14 and FIG. 15 is used as a general stem type on the inboard side. The shaft member 13b has the joining end surface 51 to be brought into abutment against the joining end surface 50 (see FIG. 4b) of the bottom portion 12a2 (short shaft section 12a3) of the cup member 12a. The outer diameter B and the inner diameter E of the joining end surface 51 are set to the equal dimensions to the outer diameter B and the inner diameter E of the joining end surface 51 of the shaft member 13a of the long stem type illustrated in FIG. 5c.

Also in this case, the inner diameter D of the joining end surface 50 of the cup member 12a is set smaller than the inner diameter E of the joining end surface 51 of the shaft member 13b. As a result, on the joining end surface 50 of the cup member 12a, the protruding surface 50a protruding to the radially inner side with respect to the inner diameter E of the joining end surface 51 of the shaft member 13b is formed. The joining end surfaces 50 and 51 having such shape are brought into abutment against each other to be welded so that the cup member 12a and the shaft member 13b are joined to each other.

The shaft member 13b is used as the general stem type on the inboard side. Accordingly, the shaft member 13b comprises a shaft section with a small length, and a sliding bearing surface 25 formed on an axial center portion thereof, and a plurality of oil grooves 26 are formed in the sliding bearing surface 25. The spline shaft Sp and the snap ring groove 48 are formed in an end portion on the side opposite to the cup member 12a side. As described above, even when there are differences in types, such as the general length stem type and the long stem type, and shaft diameters and outer peripheral shapes vary in each vehicle type, the outer diameter B of the joining end surface 51 of the shaft member 13a or 13b is set to an equal dimension.

The outer diameter B of the joining end surface 50 of the cup member 12a and the joining end surface 51 of the shaft member 13a or 13b is set to an equal dimension for each joint size. Thus, the cup member prepared for common use for each joint size, and the shaft member having a variety of specifications of the shaft section for each vehicle type can be prepared in a state before heat treatment. Further, the intermediate component of each of the cup member 12a and the shaft member 13a or 13b can be assigned with a product number for management. Even when standardizing product types of the cup member 12a, various types of the outer joint members 11 satisfying requirements can be produced quickly through combination of the cup member 12a and the shaft member 13a or 13b having a variety of specifications of the shaft section for each vehicle type. Therefore, standardization of a product type of the cup member 12a can reduce cost and alleviate a burden of production management.

The standardization of the product type of the cup member is described above by taking the differences in types, such as the general length stem type and the long stem type, as an example for easy understanding, but the present invention is not limited thereto. The same applies to standardization of the product type of the cup member for shaft members having a variety of specifications of the shaft section for each vehicle type among the general length stem types, and for shaft members having a variety of specifications of the shaft section for each vehicle type among the long stem types.

Figure 16:
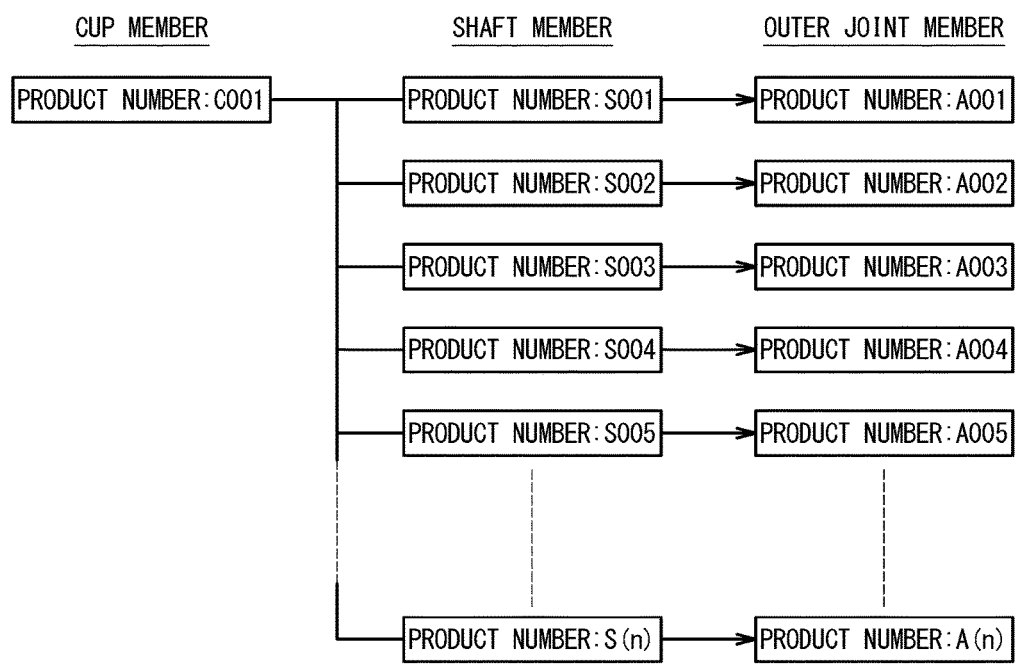
FIG. 16 is a block line diagram for illustrating an example of standardization of a product type of the cup member.

An example of standardization of a product type of the cup member is illustrated in FIG. 16.

As illustrated in FIG. 16, the cup member is prepared for common use for one joint size, and is assigned with, for example, a product number C001 for management. In contrast, the shaft member has a variety of specifications of the shaft section for each vehicle type, and is assigned with, for example, a product number S001, S002, or S(n) for management. For example, when the cup member assigned with the product number C001 and the shaft member assigned with the product number S001 are combined and welded to each other, the outer joint member assigned with a product number A001 can be produced.

Thus, owing to standardization of a product type of the cup member, it is possible to reduce cost and to alleviate a burden of production management. In the standardization of a product type, the cup member is not limited to one type for one joint size, that is, not limited to one type assigned with a single product number. For example, the cup member comprises cup members of a plurality of types (assigned with a plurality of product numbers, respectively) that are prepared for one joint size based on different specifications of a maximum operating angle, and are each prepared so that the outer diameter B of the joining end surface of each of those cup members has an equal dimension.

Next, a second embodiment of the outer joint member is described with reference to FIG. 17a to FIG. 17c and FIG. 18.

Figure 18:
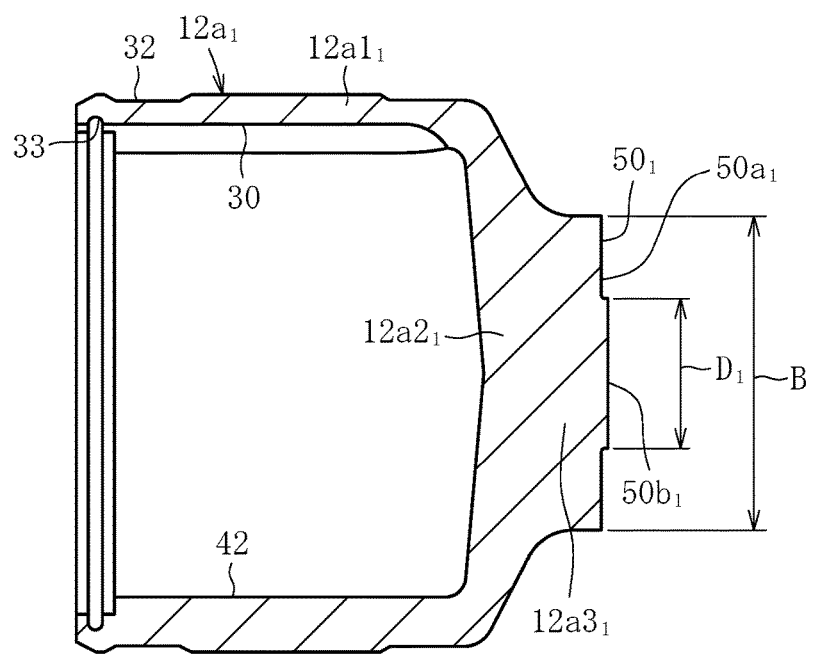

FIG. 17a is a partial sectional front view of the outer joint member. FIG. 17b is an enlarged view of a portion "b" of FIG. 17a. FIG. 17c is a view for illustrating a state before welding in FIG. 17b. FIG. 18 is a vertical sectional view for illustrating the cup member before welding.

A form of a protruding surface formed on a joining end surface of the cup member of this second embodiment is different from that in the first embodiment described above. Other configurations are the same as those in the first embodiment. Thus, parts that have the same function as those of the first embodiment are denoted by the same reference symbols except for the subscripts, and overlapping description is omitted. The shaft member 13a side is also not different from that of the first embodiment (FIG. 2a to FIG. 2c). That is, as illustrated in FIG. 17a to FIG. 17c, the recess (52: see FIG. 2a to FIG. 2c) is formed on the end surface of the shaft member 13a, and the joining end surface 51 is formed into an annular surface having the inner diameter E.

As illustrated in FIG. 17c and FIG. 18, a joining end surface $50_1$ formed on a short shaft section $12a3_1$ of a cup member $12a_1$ is annular, and a projecting portion $50b_1$ is formed on the radially inner side. In this case, a diameter $D_1$ of the annular joining end surface $50_1$ on the radially inner side corresponds to the inner diameter D of the joining end surface 50 of the cup member 12a of the first embodiment of the outer joint member. A portion of the joining end surface $50_1$ on the radially inner side protrudes toward the radially inner side with respect to the inner diameter E of the joining end surface 51 of the shaft member 13a. This protruding portion is referred to as a protruding surface $50a_1$ as in the first embodiment.

The cup member $12a_1$ can be formed by turning an end surface of the short shaft section $12a3'$ of the preform $12a'$ (FIG. 4a) for the cup member of the first embodiment after ironing at only a portion of the joining end surface $50_1$ on the radially outer side. Thus, the time for the turning can be reduced, with good material yield. As a matter of course, the protruding portion $50b_1$ on the radially inner side can also be subjected to turning. However, the number of steps can be reduced by maintaining the forged surface as it is. A height of the protruding portion $50b_1$ is set smaller than a depth of the recess 52 (see FIG. 2a to FIG. 2c) so as to prevent interference with the abutment of the joining end surfaces $50_1$ and 51.

Other configurations and operations, that is, the overview of the respective steps, the states of the cup member and the shaft member in the main processing steps, the preparation of the cup member for common use, the welding method, the ultrasonic flaw detection, the standardization of the product type, the configuration of the outer joint member, and the like as described above in relation to the first embodiment of the outer joint member are also applicable to the second embodiment of the outer joint member.

Herein, with regard to setting of the outer diameter B of the joining end surface 50 or 50$_1$ of the cup member 12*a* or 12*a*$_1$ and the protruding surface 50*a* or 50*a*$_1$ to the equal dimension for each joint size, the cup member 12*a* or 12*a*$_1$ is not limited to one type for one joint size, that is, not limited to one type assigned with a single product number.

For example, the cup member encompasses cup members of a plurality of types (assigned with a plurality of product numbers, respectively) that are prepared for one joint size based on different specifications of a maximum operating angle, and are also prepared so that the outer diameters of the above-mentioned joining end surfaces of the cup members are set to equal dimensions and that the protruding surfaces are formed into the same shape.

In addition, the cup member encompasses, for example, cup members of a plurality of types (assigned with a plurality of product numbers, respectively) that are prepared for one joint size in order to achieve management of the cup members in a plurality of forms including intermediate components before heat treatment and finished components subjected to heat treatment in consideration of the joint function, the circumstances at the manufacturing site, the productivity, and the like, and are also prepared so that the outer diameters of the above-mentioned joining end surfaces of the cup members are set to equal dimensions and that the protruding surfaces are formed into the same shape.

Further, setting the outer diameter B of the joining end surface 50 or 50$_1$ of the cup member 12*a* or 12*a*$_1$ to an equal dimension for each joint size, or forming the protruding surface 50*a* or 50*a*$_1$ into the same shape for each joint size may be applied also to different types of constant velocity universal joints. For example, setting outer diameters of the joining end surfaces of a tripod type constant velocity universal joint and a double-offset constant velocity universal joint to equal dimensions, and forming the protruding surfaces into the same shape on the inboard side are also encompassed. Further, setting outer diameters of the joining end surfaces of a Rzeppa type constant velocity universal joint and an undercut-free constant velocity universal joint to equal dimensions, and forming the protruding surfaces into the same shape on the outboard side are also encompassed. Further, setting the outer diameters of the joining end surfaces of the constant velocity universal joints on the inboard side and the outboard side to equal dimensions, and forming the protruding surfaces into the same shape on the inboard side and the outboard side are also possible.

At least one of the cup member 12*a* or 12*a*$_1$ and the shaft member 13*a* or 13*b* before welding may be prepared as an intermediate component without performing heat treatment. In this case, heat treatment and finishing such as grinding and quenched-steel cutting work are preformed after welding. Thus, this configuration is suited to the cup members 12*a* and 12*a*$_1$ and the shaft members 13*a* and 13*b* having such shapes and specifications that the hardness of the heat-treated portion may be affected by temperature rise at the periphery due to heat generated during welding after heat treatment. The intermediate component is assigned with a product number for management.

Further, at least one of the cup member 12*a* or 12*a*$_1$ and the shaft member 13*a* or 13*b* before welding may be prepared as a finished component subjected to heat treatment. The finished component subjected to heat treatment is a finished component subjected to the heat treatment and the finishing such as grinding after the heat treatment or quenched-steel cutting work. In this case, it is possible to obtain the cup member 12*a* or 12*a*$_1$ prepared as the finished component for common use for each joint size, and the shaft members having a variety of specifications of the shaft section for each vehicle type. Thus, the cup members and the shaft members are each assigned with a product number for management. Therefore, the cost is significantly reduced through the standardization of a product type of the cup members 12*a* and 12*a*$_1$, and the burden of production management is significantly alleviated.

Further, the cup members 12*a* and 12*a*$_1$ prepared for common use and the shaft members 13*a* and 13*b* having a variety of specifications of the shaft section can be manufactured separately until the cup members and the shaft members are formed into the finished components subjected to the finishing such as forging, turning, heat treatment, grinding, and quenched-steel cutting work. Further, as well as reduction of setups and the like, the enhancement of productivity is achieved. However, the cup members 12*a* and 12*a*$_1$ and the shaft members 13*a* and 13*b* as the finished components are not limited to members subjected to finishing such as the grinding after the heat treatment or the quenched-steel cutting work as described above. The cup members 12*a* and 12*a*$_1$ and the shaft members 13*a* and 13*b* assuming a state after completion of heat treatment and before being subjected to the finishing are encompassed.

Figure 19:
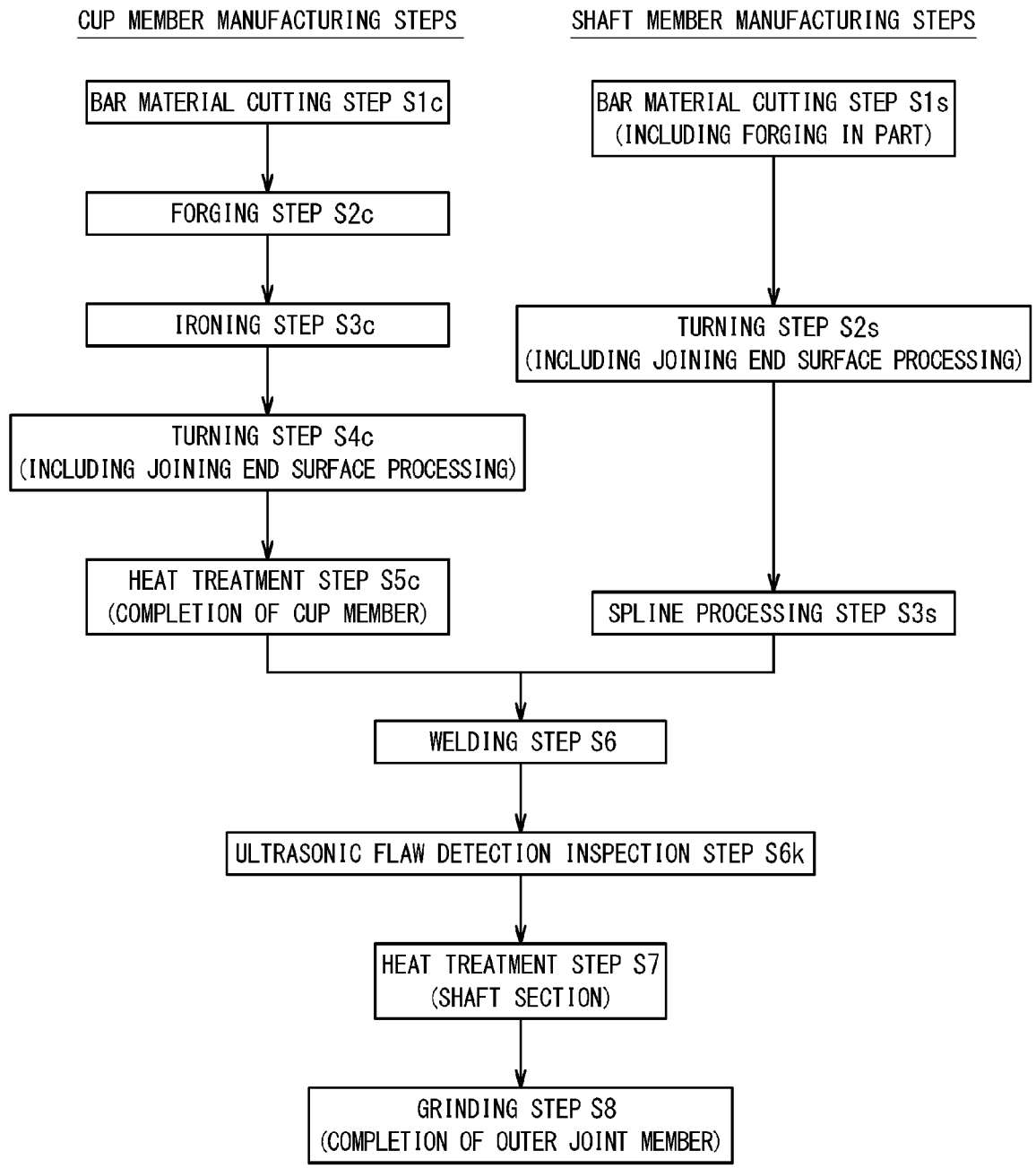
FIG. 19 is a block line diagram for illustrating a second embodiment of a method of manufacturing an outer joint member.

FIG. 19 is an illustration of a second embodiment of a manufacturing method of the outer joint member.

In the second embodiment, the heat treatment step for the cup member, which is involved in the heat treatment step S7 in FIG. 3, is provided before the welding step S6 and named "heat treatment step S5*c*", to thereby prepare the cup member as a finished product. Other than this point, the matters described above in relation to the first embodiment of the manufacturing method, that is, the overview of the respective steps, the states of the cup member and the shaft member in the main processing steps, the preparation of the cup member for common use, the welding method, the ultrasonic flaw detection, the standardization of the product type, the configuration of the outer joint member, and the like are also applicable to the second embodiment.

As illustrated in FIG. 4*b*, the cup member 12*a* has a shape extending from the joining end surface 50 to the large-diameter cylindrical portion 12*a*1 via the bottom portion 12*a*2, and the portions to be subjected to heat treatment that involves quenching and tempering are the track grooves 30 and the cylindrical inner peripheral surface 42 located at the inner periphery of the cylindrical portion 12*a*1. Therefore, the cup member 12*a* generally has no risk of thermal effect on the heat-treated portion during the welding. For this reason, the cup member 12*a* is subjected to heat treatment before the welding to be prepared as a finished product. Such manufacturing steps are suitable in practical use.

The cup member 12*a* is subjected to heat treatment for preparing the cup member 12*a* as a finished product, and is therefore assigned with a product number indicating a finished product for management. Thus, the standardization of the product type of the cup member 12*a* remarkably reduces the cost and alleviates the burden of production management. Further, the cup member 12*a* can be manufactured solely until the cup member 12*a* is completed as a finished product through the forging, turning, and heat treatment. Thus, the productivity is enhanced by virtue of reduction of setups and the like as well.

With regard to FIG. 16 for illustrating the example of standardization of the product type of the cup member described above in relation to the first embodiment of the manufacturing method, only the product number of the cup member in FIG. 16 is changed to the product number indicating a finished product, whereas the product numbers of the shaft member and the outer joint member are the same as those of the first embodiment of the manufacturing method. Therefore, description thereof is omitted herein.

Figure 20:
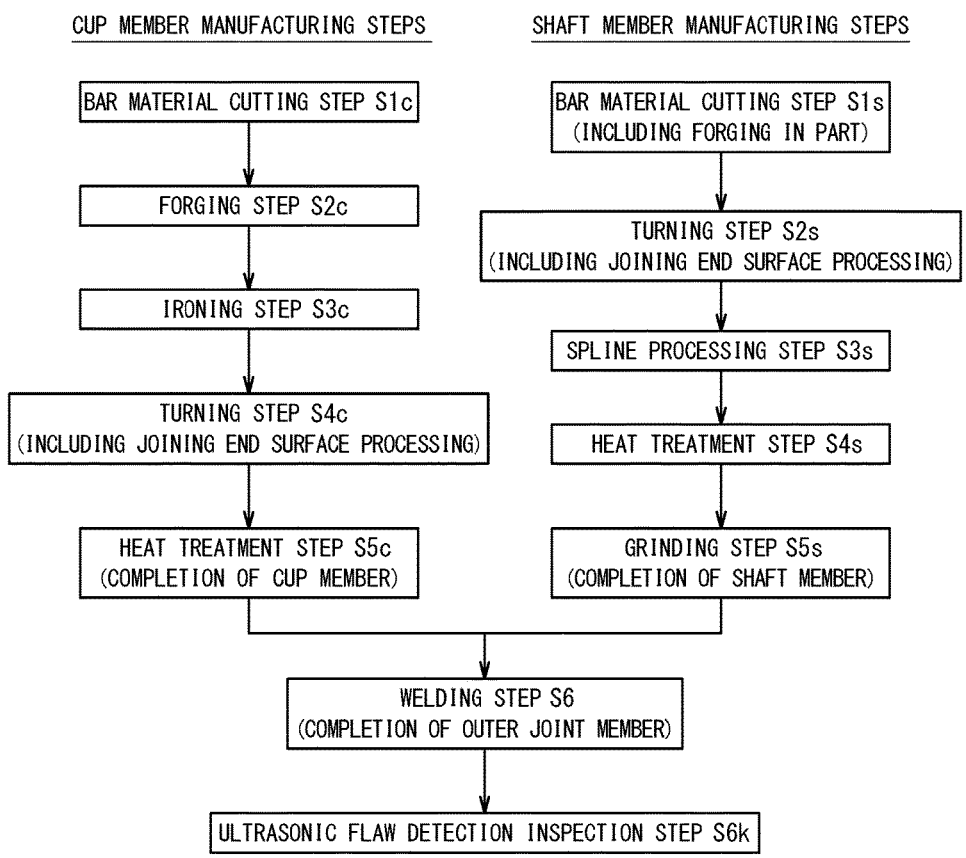
FIG. 20 is a block line diagram for illustrating a third embodiment of the method of manufacturing the outer joint member.

FIG. 20 is an illustration of a third embodiment of a manufacturing method of the outer joint member.

In the third embodiment of the manufacturing method, the heat treatment steps for the cup section and the shaft section, which are involved in the heat treatment step S7 in FIG. 3 described above in relation to the first embodiment, and the grinding step S8 for the shaft section in FIG. 3 are provided before the welding step S6 in the sequence and named "heat treatment step S5c for cup member", "heat treatment step S4s for shaft member", and "grinding step S5s". Thus, both the cup member and the shaft member are prepared as finished products. Other matters, that is, the overview of the respective steps, the states of the cup member and the shaft member in the main processing steps, the preparation of the cup member for common use, the welding method, the ultrasonic flaw detection, the standardization of the product type, the configuration of the outer joint member, and the like described in relation to the first embodiment are also applicable to the third embodiment of the manufacturing method.

After the spline processing step S3s, a hardened layer having a hardness of approximately from 50 HRC to 62 HRC is formed in a predetermined range of the outer peripheral surface of the shaft member by induction quenching in the heat treatment step S4s. Heat treatment is not performed on a predetermined portion in the axial direction, which includes the joining end surface 51. The heat treatment for the cup member, the assignment of the product number, and the like are the same as those of the second embodiment on the manufacturing method, and redundant description is therefore omitted herein.

After the heat treatment step S4s, the shaft member is transferred to the grinding step S5s so that the bearing mounting surface 14 and the like are finished. Thus, the shaft member is obtained as a finished product. Then, the shaft member is assigned with a product number indicating a finished product for management. The manufacturing steps of the third embodiment are suitable in a case of a cup member and a shaft member having shapes and specifications with no risk of thermal effect on the heat-treated portion during the welding.

In the manufacturing steps of the third embodiment, both the cup member and the shaft member can be assigned with product numbers indicating finished products for management. Thus, the standardization of the product type of the cup member further remarkably reduces the cost and alleviates the burden of production management. Further, the cup member and the shaft member can be manufactured independently of each other until the cup member and the shaft member are completed as finished products through the forging, turning, heat treatment, grinding after heat treatment, and the like. Thus, the productivity is further enhanced by virtue of reduction of setups and the like as well.

In the case of the third embodiment of the manufacturing method, with regard to FIG. 16 for illustrating the example of standardization of the product type of the cup member described above in relation to the first embodiment, the product numbers of the cup member and the shaft member in FIG. 16 are changed to the product numbers indicating finished products. The outer joint member is the same as that of the first embodiment of the manufacturing method. Therefore, description thereof is omitted herein. Note that, the cup member and the shaft member to be prepared as finished products are not limited to the cup member and the shaft member subjected to finishing such as the above-mentioned grinding after heat treatment or cutting after quenching, and encompass a cup member and a shaft member in a state in which the heat treatment is completed while the finishing is uncompleted.

As described with regard to the standardization of the product type, the cup member is not limited to one type for one joint size, that is, not limited to one type assigned with a single product number. The cup member encompasses, for example, cup members of a plurality of types (assigned with a plurality of product numbers, respectively) that are prepared for one joint size based on different specifications of a maximum operating angle, and are also prepared so that the outer diameters B of the above-mentioned joining end surfaces of the cup members are set to equal dimensions. In addition, the cup member encompasses, for example, cup members of a plurality of types (assigned with a plurality of product numbers, respectively) that are prepared for one joint size in order to achieve management of the cup members in a plurality of forms including intermediate components before heat treatment and finished components in consideration of the joint function, the circumstances at the manufacturing site, the productivity, and the like, and are also prepared so that the outer diameters B of the above-mentioned joining end surfaces of the cup members are set to equal dimensions.

Next, a third embodiment of the outer joint member is described with reference to FIG. 21 and FIG. 22.

Herein, parts that have the same function as those of the first embodiment of the outer joint member are denoted by the same reference symbols, and only main points are described.

Figure 21:
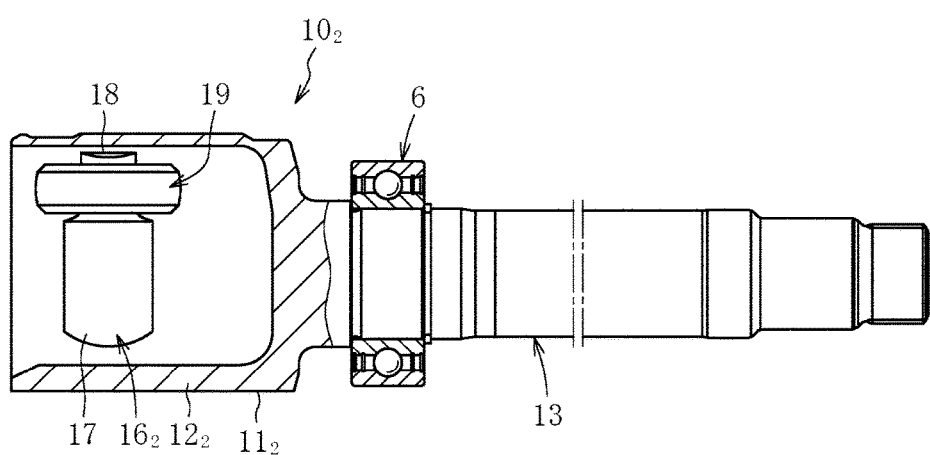
FIG. 21 is a partial sectional front view for illustrating a constant velocity universal joint of the third embodiment of the outer joint member.

A plunging type constant velocity universal joint $10_2$ illustrated in FIG. 21 is a tripod type constant velocity universal joint (TJ), and comprises an outer joint member $11_2$, an inner joint member $16_2$, and rollers 19 serving as torque transmitting elements. The outer joint member $11_2$ comprises a cup section $12_2$ and the long stem section 13 that extends from a bottom of the cup section $12_2$ in the axial direction. The inner joint member $16_2$ comprises a tripod member 17 comprising three equiangular leg shafts 18 configured to support the rollers 19 in a freely rotatable manner, and is housed along an inner periphery of the cup section $12_2$ of the outer joint member $11_2$. The rollers 19 are arranged between the outer joint member $11_2$ and the inner joint member $16_2$, and configured to transmit torque therebetween.

Similarly to the first embodiment of the outer joint member, the inner ring of the support bearing 6 is fixed to the outer peripheral surface of the long stem section 13, and the outer ring of the support bearing 6 is fixed to the transmission case with the bracket (not shown). The outer joint member $11_2$ is supported by the support bearing 6 in a freely rotatable manner, and thus the vibration of the outer joint member $11_2$ during driving or the like is prevented as much as possible.

Figure 22:
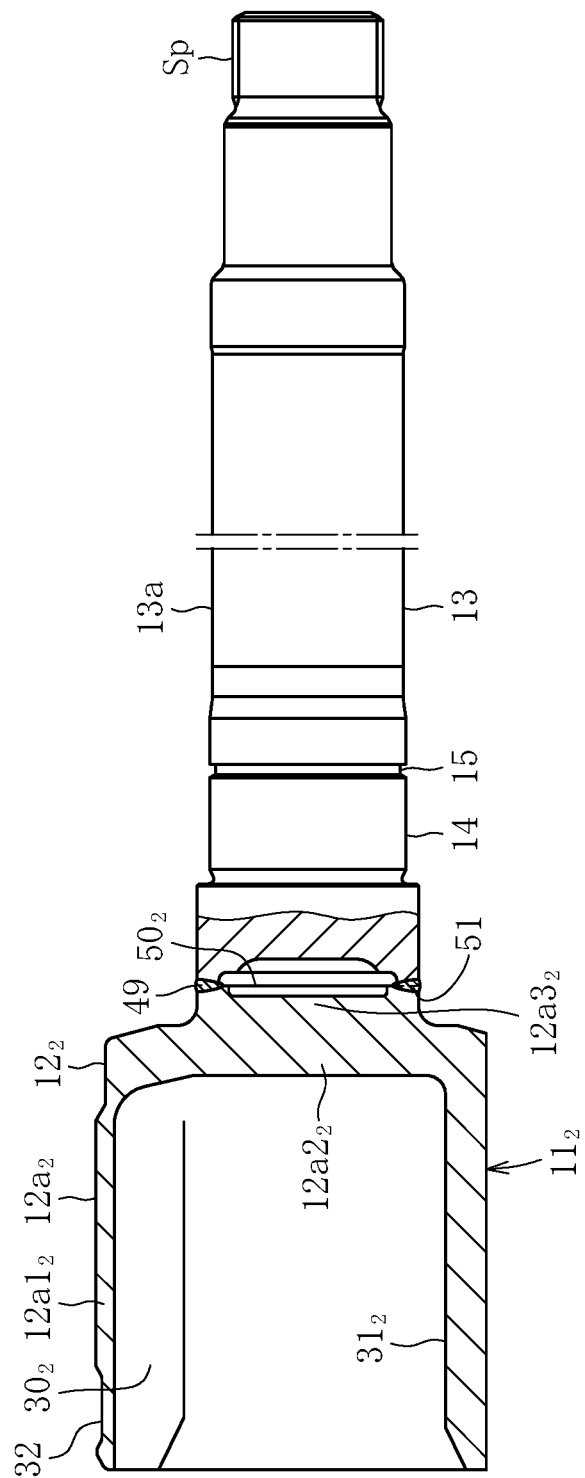
FIG. 22 is a partial sectional front view of the outer joint member of FIG. 21.
Figure 23:
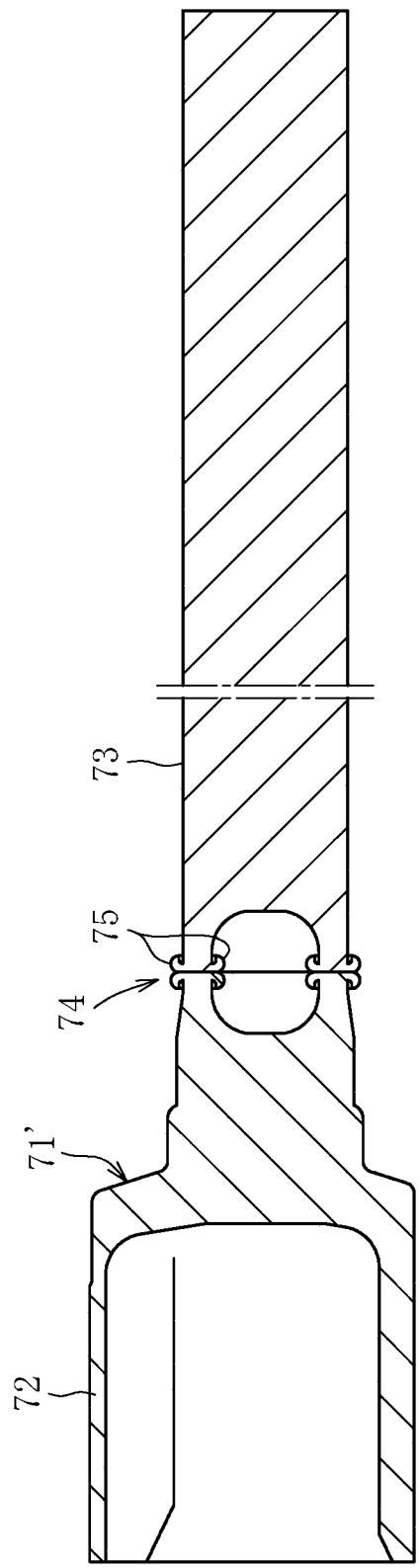
FIG. 23 is a vertical sectional view of an intermediate product of an outer joint member for illustrating a related art.
Figure 24:
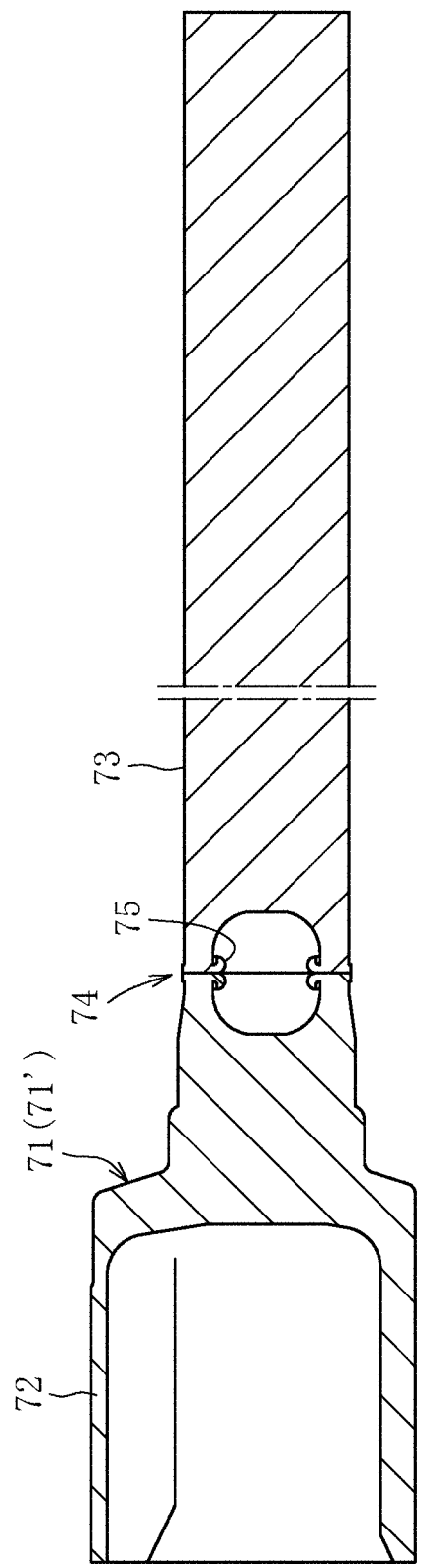
FIG. 24 is a vertical sectional view of the outer joint member for illustrating the related art.
Figure 25:
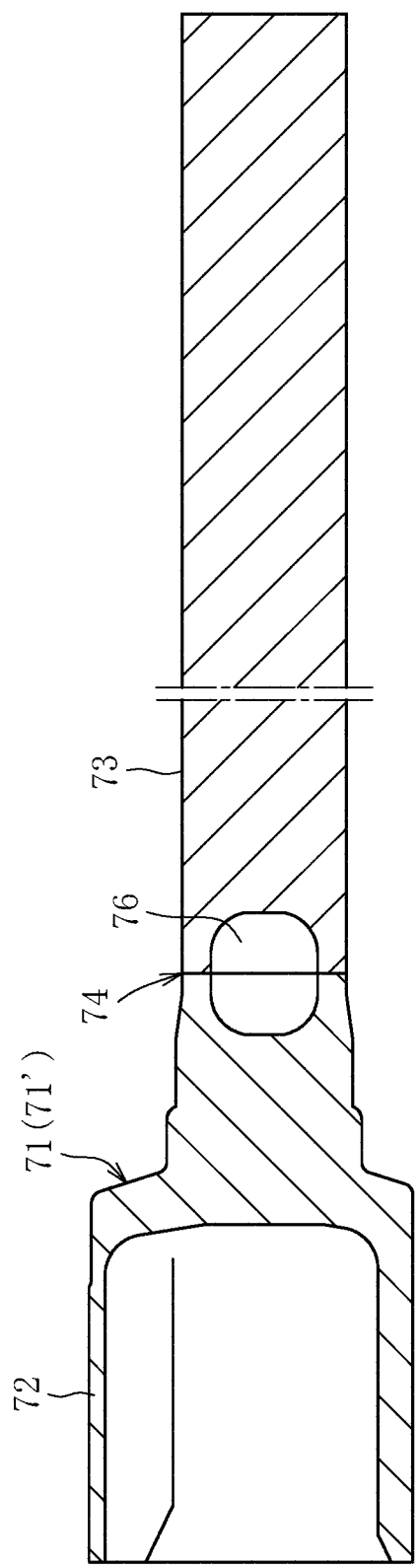
FIG. 25 is a vertical sectional view of an outer joint member for illustrating another related art.

As illustrated in FIG. 22, the outer joint member $11_2$ comprises a cup section $12_2$ and the long stem section 13. The cup section $12_2$ has a bottomed cylindrical shape that is opened at one end, and has track grooves $30_2$, on which the rollers 19 are caused to roll, formed at three equiangular positions on an inner peripheral surface $31_2$. The long stem section 13 extends from the bottom of the cup section $12_2$ in the axial direction and comprises the spline shaft Sp serving as the torque transmitting coupling portion formed at the outer periphery of the end portion on the side opposite to the cup section $12_2$.

The outer joint member $11_2$ is formed by welding the cup member $12a_2$ serving as the cup section $12_2$ and the shaft member $13a$ serving as the long stem section $13$ to each other.

The cup member $12a_2$ is an integrally-formed product having a cylindrical portion $12a1_2$ and a bottom portion $12a2_2$, and has track grooves $130$ and an inner peripheral surface $131$ formed at the inner periphery of the cylindrical portion $12a1_2$. A short shaft section $12a3_2$ is formed at the bottom portion $12a2_2$. A boot mounting groove $32$ is formed at an outer periphery of the cup member $12a_2$ on the opening side.

In the shaft member $13a$, the bearing mounting surface $14$ and the snap ring groove $15$ are formed at the outer periphery on the cup member $12a_2$ side, and the spline shaft Sp is formed at an end portion on the side opposite to the cup member $12a_2$.

A joining end surface $50_2$ formed at the short shaft section $12a3_2$ of the bottom portion $12a_1$ of the cup member $12a_2$ and the joining end surface $51$ formed at the end portion of the shaft member $13a$ on the cup member $12a_2$ side are brought into abutment against each other, and are welded to each other by radiating an electron beam from the radially outer side. As is well known, the welded portion $49$ comprises metal that is molten and solidified during welding, that is, the molten metal, and the heat-affected portion in the periphery thereof.

Similarly to the first embodiment of the outer joint member, the outer diameters B of the joining end surface $50_2$ and the joining end surface $51$ are set to equal dimensions for each joint size. The welded portion $49$ is formed on the cup member $12a_2$ side with respect to the bearing mounting surface $14$ of the shaft member $13a$, and hence the bearing mounting surface $14$ and the like can be processed in advance so that post-processing after welding can be omitted. Further, due to the electron beam welding, burrs are not generated at the welded portion. Thus, post-processing for the welded portion can also be omitted, which can reduce the manufacturing cost.

The matters described in relation to the first and second embodiments of the outer joint member and the first to third embodiments of the manufacturing method are also applicable to the third embodiment of the outer joint member.

The effects of the above-mentioned embodiments of the present invention are summarized and described below.

According to the embodiments, the method of butt-welding comprises, with the cup member $12a$, $12a_1$, or $12a_2$ being a first workpiece and the shaft member $13a$ or $13b$ being a second workpiece, bringing a solid shaft-shaped end portion of the first workpiece $12a$, $12a_1$, or $12a_2$ and a solid shaft-shaped end portion of the second workpiece $13a$ or $13b$ into abutment against each other, and radiating a high energy intensity beam from a radially outer side to perform butt-welding. The second workpiece $13a$ or $13b$ has the recess $52$ on the joining end surface $51$, and the first workpiece $12a$, $12a_1$, or $2a_2$ has the joining end surface $50$, $50_1$, or $50_2$ protruding toward the radially inner side with respect to the inner diameter E of the joining end surface $51$ of the second workpiece $13a$ or $13b$.

The joining end surface $50$ or $50_2$ of the first workpiece $12a$ or $12a_2$ has the recessed portion $50b$ having a diameter smaller than a diameter of the recess $52$. With this, the joining end surface $50$ or $50_2$ is formed into an annular surface, and hence time required for turning can be reduced.

Alternatively, the joining end surface $50_1$ of the first workpiece $12a_1$ has, at a center portion thereof, the protruding portion $50b_1$ which has a diameter smaller than a diameter of the recess $52$ and which has a height smaller than a depth of the recess $52$. Also in this case, the joining end surface $50_1$ is formed into an annular surface. Thus, through performing turning only for the joining end surface $50_1$ and maintaining the forged surface on the protruding portion $50b_1$ on the radially inner side, the processing time can be reduced with a good material yield.

The recess $52$ may be formed by cutting work, or may be formed during forging. As compared to the former, the latter is more advantageous in terms of reduction in number of steps and in terms of a material yield.

The protruding surface $50a$ or $50a_1$ of the joining end surface $50$, $50_1$, or $50_2$ may have the same shape for each joint size. Thus, workability for the cup members $12a$, $12a_1$, and $12a_2$ to be standardized in product type is enhanced. Therefore, the productivity can be further enhanced, and the burden of product management can be further reduced.

Further, the protruding surface $50a$ or $50a_1$ is formed on the joining end surface $50$, $50_1$, or $50_2$ of the cup member $12a$, $12a_1$, or $12a_2$. With this, at the time of performing the ultrasonic flaw detection for the welded portion $49$, an angle probe may allow the ultrasonic waves to enter from the surface side of the shaft member $13a$ or $13b$ having a small shaft diameter. Thus, the inspection can easily be performed.

The embodiments of the present invention are described above with reference to the attached drawing. However, the present invention is not limited to the embodiments described herein and illustrated in the attached drawings. The present invention can be carried out with various modifications within the range of not departing from the scope of claims.

For example, description is made of the case where the protruding surface is formed on the radially inner side of the joining end surface of the cup member. However, in contrast, the protruding surface may be formed on the radially inner side of the joining end surface of the shaft member. The ultrasonic flaw detection in this case may be performed by allowing the ultrasonic waves to enter from the surface side of the cup member.

The case of employing the electron beam welding is described as an example. However, the present invention is applicable not only to the case of the electron beam welding but also to the case of employing laser welding or other welding through use of a high energy intensity beam.

Further, the double-offset type constant velocity universal joint and the tripod type constant velocity universal joint are exemplified as the plunging type constant velocity universal joint. However, the present invention is also applicable to an outer joint member of a cross-groove type constant velocity universal joint or other plunging type constant velocity universal joint, and to an outer joint member of a fixed type constant velocity universal joint. Further, the case of applying the present invention to the outer joint member of the constant velocity universal joint constructing a drive shaft is described as an example. However, the present invention is also applicable to an outer joint member of a constant velocity universal joint constructing a propeller shaft.

REFERENCE SIGNS LIST 10 plunging type constant velocity universal joint
11 outer joint member
12 cup section
12a cup member 12a1 cylindrical portion
12a2 bottom portion
12a3 short shaft section
13 long shaft section
13a shaft member
14 bearing mounting surface
16 inner joint member
17 tripod member
19 torque transmitting element (roller)
30 track groove
40 track groove
41 torque transmitting element (ball)
42 inner peripheral surface
49 welded portion
50 joining end surface of cup member
50a protruding surface
50b recessed portion
50b1 projecting portion
51 joining end surface of shaft member
52 recess
53 inner diameter portion (of joining end surface 51)
100 welding apparatus
101 electron gun
108 case
109 vacuum pump
111 sealed space
120 ultrasonic flaw-detection apparatus
121 base
122 water bath
123 workpiece support
124 workpiece holding member
125 rotary drive device
135 pressing device
136 drive positioning device
147 probe

The invention claimed is:

1. A method of manufacturing an outer joint member of a constant velocity universal joint, the method comprising:
bringing a solid shaft-shaped end portion of a cup member and a solid shaft-shaped end portion of a shaft member into abutment against each other; and
radiating a high energy intensity beam from a radially outer side to perform butt welding, wherein
the shaft member has a joining end surface and a recess formed on a radially inner side of the joining end surface of the shaft member,
the cup member has a joining end surface protruding toward a radially inner side with respect to an inner diameter of the joining end surface of the shaft member and a protruding portion provided on a radially inner side with respect to the joining end surface of the cup member,
the shaft member is formed by upset forging,
the cup member is formed by forging,
the joining end surface and the protruding portion of the cup member are formed by performing turning on only an annular region of an end surface of the cup member, and
the butt welding is performed by bringing the joining end surface of the cup member and the joining end surface of the shaft member into abutment against each other.

2. The method of manufacturing an outer joint member of a constant velocity universal joint according to claim 1, wherein the protruding portion has a diameter that is smaller than a diameter of the recess and has a height that is smaller than a depth of the recess.

3. The method of manufacturing an outer joint member of a constant velocity universal joint according to claim 1, wherein the joining end surface of the shaft member is formed by cutting.

4. The method of manufacturing an outer joint member of a constant velocity universal joint according to claim 1, wherein the recess of the shaft member is formed by forging.

5. The method of manufacturing an outer joint member of a constant velocity universal joint according to claim 2, wherein the joining end surface of the shaft member and an inner diameter portion of the joining end surface of the shaft member are subjected to cutting.

6. The method of manufacturing an outer joint member of a constant velocity universal joint according to claim 1, wherein the protruding portion has a forged surface.

7. The method of manufacturing an outer joint member of a constant velocity universal joint according to claim 2, wherein the joining end surface of the shaft member is formed by cutting.

8. The method of manufacturing an outer joint member of a constant velocity universal joint according to claim 2, wherein the recess of the shaft member is formed by forging.

9. The method of manufacturing an outer joint member of a constant velocity universal joint according to claim 3, wherein the protruding portion has a forged surface.

10. The method of manufacturing an outer joint member of a constant velocity universal joint according to claim 4, wherein the protruding portion has a forged surface.

11. The method of manufacturing an outer joint member of a constant velocity universal joint according to claim 5, wherein the protruding portion has a forged surface.

12. The method of manufacturing an outer joint member of a constant velocity universal joint according to claim 8, wherein the protruding portion has a forged surface.

* * * * *